(12) United States Patent
Aboytes

(10) Patent No.: US 11,141,178 B2
(45) Date of Patent: Oct. 12, 2021

(54) SYSTEMS, DEVICES, AND METHODS FOR OBSTRUCTION RETRIEVAL AND TREATMENT

(71) Applicant: Maria G. Aboytes, Palo Alto, CA (US)

(72) Inventor: Maria G. Aboytes, Palo Alto, CA (US)

(*) Notice: Subject to any disclaimer, the term of this patent is extended or adjusted under 35 U.S.C. 154(b) by 135 days.

(21) Appl. No.: 16/490,528

(22) PCT Filed: Mar. 2, 2018

(86) PCT No.: PCT/US2018/020608
§ 371 (c)(1),
(2) Date: Aug. 31, 2019

(87) PCT Pub. No.: WO2018/160935
PCT Pub. Date: Sep. 7, 2018

(65) Prior Publication Data
US 2020/0121335 A1     Apr. 23, 2020

Related U.S. Application Data

(60) Provisional application No. 62/466,799, filed on Mar. 3, 2017.

(51) Int. Cl.
*A61B 17/221*     (2006.01)
*A61B 34/32*      (2016.01)
(Continued)

(52) U.S. Cl.
CPC ............ *A61B 17/221* (2013.01); *A61B 34/32* (2016.02); *A61B 2017/00867* (2013.01);
(Continued)

(58) Field of Classification Search
CPC ...... A61B 2090/3966; A61B 2090/363; A61B 2018/00386; A61B 2018/00345;
(Continued)

(56) References Cited

U.S. PATENT DOCUMENTS

2009/0198269 A1*  8/2009  Hannes ................ A61B 17/221
                                                      606/200
2009/0299393 A1* 12/2009  Martin ................. A61B 17/221
                                                      606/159

(Continued)

*Primary Examiner* — Jocelin C Tanner
(74) *Attorney, Agent, or Firm* — Steven Stupp

(57) ABSTRACT

Systems, devices, and methods for removing and/or treating obstructions in the vascular channels, such as blood clots, are provided. The systems may include a capture sock device including a shaft defining a lumen; and a mouth coupled to the shaft. The mouth includes a distal end portion defining a distal opening and is sized and configured to move between a collapsed configuration and an expanded configuration within a body channel. The mouth is formed of a mesh having porosity large enough to allow blood flow to pass through it but small enough to prevent an obstruction or a fragment of the obstruction from escaping from the mouth back into the body channel. In some embodiments, the mesh is folded to create at least two mesh layers at least at the distal opening to create a smooth atraumatic edge. In some embodiments, the system further includes a trap and/or retriever assembly.

20 Claims, 22 Drawing Sheets

(51) Int. Cl.
*A61B 90/00* (2016.01)
*A61B 17/00* (2006.01)
*A61B 17/22* (2006.01)

(52) U.S. Cl.
CPC .............. *A61B 2017/22038* (2013.01); *A61B 2017/22061* (2013.01); *A61B 2017/22079* (2013.01); *A61B 2090/363* (2016.02); *A61B 2090/3966* (2016.02)

(58) Field of Classification Search
CPC .... A61B 2018/0025; A61B 2018/0022; A61B 2017/22094; A61B 2017/22084; A61B 2017/22079; A61B 2017/22061; A61B 2017/22038; A61B 2017/22034; A61B 2017/00867; A61B 34/32; A61B 18/1492; A61B 17/221; A61B 17/22022; A61B 17/2215
See application file for complete search history.

(56) References Cited

U.S. PATENT DOCUMENTS

| | | | | |
|---|---|---|---|---|
| 2010/0268264 A1* | 10/2010 | Bonnette | ............... | A61F 2/0108 606/200 |
| 2012/0059356 A1* | 3/2012 | di Palma | ............... | A61B 17/221 604/509 |
| 2014/0276403 A1* | 9/2014 | Follmer | ........... | A61B 17/22032 604/103.02 |
| 2018/0042628 A1* | 2/2018 | Panian | ............. | A61B 17/22031 |
| 2020/0029984 A1* | 1/2020 | Wang | ................ | A61B 17/1204 |

\* cited by examiner

SYSTEMS, DEVICES, AND METHODS FOR OBSTRUCTION RETRIEVAL AND TREATMENT

CROSS-REFERENCE TO RELATED APPLICATIONS

This application claims priority under 35 U.S.C. 371 to International Application No. PCT/US18/20608, "Systems, Devices, and Methods for Obstruction Retrieval and Treatment," by Maria G. Aboytes, filed on Mar. 2, 2018, which claims priority to U.S. Provisional Patent Application Ser. No. 62/466,799, entitled "Systems, Devices and Methods for Clot Retrieval and Treatment," by Maria G. Aboytes, filed Mar. 3, 2017, the contents of both of which are herein incorporated by reference in their entirety.

TECHNICAL FIELD

The present disclosure relates generally to medical systems, devices, and methods, and more particularly to systems, devices, and methods for removing and/or treating obstructions (e.g., blood clots) in the vascular channels (e.g., blood vessels).

BACKGROUND

Nearly 800,000 (approximately 795,000) people in the United States have a stroke every year. 87% of strokes are classified as ischemic. Ischemic strokes occur as a result of an obstruction within a blood vessel supplying blood to the brain. The primary condition for this type of obstruction is the development of fatty deposits lining the vessel walls. This condition is called atherosclerosis. These fatty deposits can cause two types of obstruction: 1) cerebral thrombosis and cerebral embolism. Cerebral thrombosis refers to a thrombus (blood clot) that develops at the clogged part of the vessel. Cerebral embolism refers generally to a blood clot that forms at another location in the circulatory system, usually the heart and large arteries of the upper chest and neck. A portion of the blood clot breaks loose, enters the bloodstream, and travels through the brain's blood vessels until it reaches vessels too small to let it pass. A second important cause of embolism is an irregular heartbeat, known as atrial fibrillation. It creates conditions where clots can form in the heart, dislodge, and travel to the brain.

Various strategies and devices have been developed to treat vascular obstructions, such as clots, plaque, emboli, or thrombus. For example, some of these devices dispense thrombolytic agents to the occluded vasculature and/or physically disrupt and dislodge the occluding thrombus. Also, the use of inflatable balloons to remove emboli has been practiced for many years. However, clots occurring in tortuous and narrowed vessels area difficult to remove using balloon catheters. Other known devices for increasing blood flow through an obstructed blood vessel include filter traps designed to trap emboli. Some of them are not easy to deploy, other are limited in a size of the emboli they can catch. Moreover, typically a procedure using those filter traps and similar devices takes multiple hours and may require multiple passes through the blood vessel. For example, known filter traps, after capturing clots, must move a long way through a tortuous vessel path during withdrawal. They often lose fragments of the clot and cause dislodgement of some fragments or particles of the obstruction, which then is deposited in another area, creating the potential for a new obstruction and even a new stroke in another location. In addition, in order to remove a large clot or obstruction, in many cases it is required to go back and forth within the same path multiple times (sometimes three or four times), prolonging the procedure and creating potential for more damage to the vessel.

Accordingly, there is a continuing need for improved systems, devices, and methods for treatment and/or removal of vascular obstructions that solve the above-mentioned problems.

SUMMARY

Generally, the present disclosure provides systems, devices, and methods for removing obstructions, for example, blood clots or plaque, and optionally at least partially dissolving them. The systems and devices of the present disclosure are configured such that any clot, tissue fragments, etc. (obstruction) which are mobilized during deployment will be trapped, therefore, preventing such fragments from entering the brain vasculature or other body channel and causing harm.

According to one aspect of the present disclosure, an obstruction removal system is provided. An obstruction removal system includes a capture sock device having a shaft and a mouth. In other embodiments, an obstruction removal system includes a capture sock device having a shaft and a mouth and a trap coupled to a distal end of a guidewire, which is coupled to the capture sock device. The trap may include one or more openings facing the capture sock device.

According to another aspect of the present disclosure, an obstruction removal system includes a capture sock device having a shaft and a mouth, and a retriever assembly. The retriever assembly includes a retriever configured to capture an obstruction (e.g., when expanded within a body channel), a proximal end of the retriever fixedly coupled to a distal end of a guidewire, and a trap fixedly coupled to the distal end of the retriever. The trap may include one or more openings facing the retriever. Any one or more of the capture sock device, the retriever, and the trap are movable between a collapsed configuration and an expanded configuration. The capture sock device and the retriever assembly are sized and configured, when positioned inside a body channel, such that the retriever with a captured obstruction may be withdrawn into the mouth of the capture sock device and that the trap may engage with the mouth of the capture sock device to form a closed chamber. The closed chamber prevents the obstruction or a fragment of the obstruction from migrating into the body channel during removal of the capture sock device and the retriever assembly from the body channel. In some embodiments, the proximal portion of the trap is tapered down. In further embodiments, the proximal portion of the trap, when positioned inside the body channel, is sized and configured to be smaller than the circumference of the distal opening of the mouth of the capture sock device thus allowing the proximal portion of the trap to fit inside while a distal portion of the trap is sized and configured to be larger than the circumference of the distal opening of the mouth of the capture sock device thereby causing the distal portion of the trap to remain outside and distal to the mouth of the capture sock device. In various embodiments, any one or more of the capture sock device, the retriever and the trap may be self-expandable when unconstrained. Also, any one or more of the capture sock device, the retriever and the trap includes or is formed of a mesh or braided structure. In some embodiments, the entire mouth or a portion of the mouth, including a distal portion, may be flared. In some embodiments, the mouth of the capture sock device includes or is formed of a mesh, and the mesh may be folded at the distal opening. The mesh may be folded once or multiple times to create a smooth atraumatic edge.

According to yet another aspect, a novel trap is provided. The trap is sized and configured to move between a collapsed configuration and an expanded configuration within the body channel, such as blood vessel. The trap includes or is formed of a mesh having porosity large enough to allow blood flow and cellular matter to pass through it but small enough to prevent an obstruction or a fragment of the obstruction from moving distally to the trap. In some embodiments, the trap is self-expanding and has a proximal portion and a distal portion, the distal portion being more rigid than a proximal portion. The trap may have one or more openings at a proximal end.

According to a further aspect, a novel capture sock device is provided. In some embodiments, the capture sock device includes a shaft having a lumen and a mouth with a distal opening. The mouth is configured to move between a collapsed configuration and an expanded configuration, and it may include or be formed of a mesh having porosity large enough to allow blood flow to pass through the mesh but small enough to prevent an obstruction or a fragment of the obstruction from escaping from the mouth into the body channel. In some embodiments, the mouth may include or be formed of a braided structure, or it may be weaved and/or laser cut to create the mesh. At least a distal portion of the mouth (or in some embodiments the entire mouth, or any portion of the mouth) is folded (e.g., one or more times) to create a plurality of layers. In some embodiments, the folded or inverted configuration includes or is formed of two layers, and in other embodiments more than two layers may be provided. Such "inverted" or "folded" design provides an edge that is smooth and atraumatic to the vessel wall. In various embodiments, a mouth of the capture sock device may be self-expanding. In further embodiments, the mouth of the capture sock device may be flared at the distal portion.

The novel capture sock device may be used with a trap of various embodiments to improve removal of obstructions, for example, removal of thrombi or other obstructions from blood vessels, including those delivering blood to the brain. For example, in various implementations, the mouth of the capture sock device may be sized and configured to complement a size and configuration of the trap such that together they may form a closed chamber, thereby preventing escape of obstructions or portions/fragments of the obstructions into the blood stream or body channel. A proximal portion of the trap may engage a distal end portion of the mouth of the capture sock device such that when engaged in that manner they together form a closed chamber preventing an obstruction, such as a clot, or any fragments of the obstruction from migrating into a body channel, such as a blood vessel, during removal of the system from the body channel. According to some embodiments, the capture sock device, the trap, or both are self-expanding. In various embodiments, a proximal portion of the trap that engages the mouth of the capture sock device may be sized, shaped, and/or configured such that its overall circumference (for example, when both the capture sock device and the trap are in their expanded configuration within a body vessel) is slightly smaller than the overall inner circumference of the mouth of the capture sock device. A fold or multiple folds of the mouth of the capture sock device, as stated elsewhere herein, will provide a smooth and atraumatic distal end or edge of the mouth of the capture sock device for easy engagement with the proximal end of the trap.

According to further aspects of the present disclosure, methods for removing obstructions, such as blood clots, are provided. In one embodiment, a method for removing obstructions from a body structure, such as a body channel is provided. One such method includes: deploying a capture sock device proximal to an obstruction site in a body channel; deploying a retriever assembly distally to the capture sock device such that a first portion of the retriever assembly is positioned in the obstruction site and a second portion of the retriever assembly is positioned distally to the obstruction site, the second portion configured to prevent the obstruction or a fragment of the obstruction from moving in a distal direction past the second portion. The method also includes moving the retriever assembly with the obstruction captured therein into the capture sock device such that the first portion of the retriever assembly containing the captured obstruction is positioned inside the capture sock device and the second portion of the retriever assembly engages a mouth of the capture sock device, (for example, within a circumference of the distal end portion or a distal opening of the mouth), thereby creating a closed chamber preventing the obstruction or a fragment of the obstruction from migrating into the body channel during removal of the capture sock device and the retriever assembly from the body channel; and removing the capture sock device and the retriever assembly from the body channel. In some embodiments, the first portion of the retriever assembly may be a retriever and a second portion of the retriever assembly may be a trap.

In various embodiments, the capture sock device may be delivered through a catheter, such as a guide catheter, using, for example, standard catherization techniques. In some embodiments, a lumen of a shaft of the capture sock device may be used to deliver a micro-catheter that may be used for deployment of the retriever assembly. The method may further include supplying electronegative current to the obstruction site to assist in dissolving the obstruction. In some embodiments, the method may include delivering clot dissolving medications, e.g., tissue plasminogen activator (tPA) or supplying oxygen to the obstruction site. In some embodiments, the method may include aspirating the obstruction or a portion of the obstruction into a capture sock device. Various steps of the method may be performed manually, or may be fully or partially automated. The methodology of the present disclosure is particularly useful in the removal of the obstructions, such as obstructions causing an ischemic stroke, especially in tortuous anatomy.

Another aspect of the present disclosure is an obstruction removal system including: a capture sock device including a mouth coupled to a shaft defining a lumen; and a trap coupled to a distal end of a guidewire, the trap including one or more openings facing the capture sock device. In some embodiments, any one or more of the capture sock device and the trap are movable between a collapsed configuration and an expanded configuration. In some embodiments, the capture sock device and the trap are sized and configured, when positioned inside a body channel, such that the trap with a captured obstruction may be withdrawn into the mouth of the capture sock device and the trap may engage with the mouth of the capture sock device to form a closed chamber. In some embodiments, the closed chamber prevents the obstruction or a fragment of the obstruction from migrating into the body channel during removal of the capture sock device and the trap from the body channel. In some embodiments, the mouth of the capture sock device has a distal end portion with a distal opening and a circumference at the distal opening, such that a proximal portion of the trap is configured to engage the circumference of the distal opening of the mouth of the capture sock device. In some embodiments, the proximal portion of the trap is tapered. In some embodiments, the proximal portion of the trap, when positioned inside the body channel, is sized and configured to be smaller than the circumference of the distal opening of the mouth of the capture sock device causing it to fit inside the mouth while a distal portion of the trap is sized and configured to be larger than the circumference of the distal opening of the mouth of the capture sock device causing it to remain outside and distal to the mouth. In some embodiments, any one or more of the capture sock device and the trap are self-expandable when unconstrained. In some embodiments, any one or more of the capture sock device and the trap comprises a mesh or braided structure. In some embodiments, at least a distal portion of the mouth of the capture sock device includes a flare or is flared. In some embodiments, in the expanded configuration, the mouth of the capture sock device is configured to contact a wall of the body channel. In some embodiments, the mouth of the capture sock device includes a mesh being folded to create two layers at the distal opening of the mouth. In some embodiments, the mesh includes or is formed of three or more layers. In some embodiments, the trap is self-expanding and includes a proximal portion and a distal portion. In some embodiments, the distal portion is more rigid than the proximal portion.

Another aspect of the present disclosure is an obstruction removal system including: a capture sock device including a mouth coupled to a shaft, such that the mouth includes a distal end portion defining a distal opening and is sized and configured to move between a collapsed configuration and an expanded configuration within a body channel; and a stent configured for delivery through the shaft and into the mouth of the capture sock device. In some embodiments, the stent is deployed within the mouth of the capture sock device to move the capture sock device from the collapsed configuration to the expanded configuration when the capture sock device is positioned within the body channel. In some embodiments, the mouth includes or is formed of a high-density mesh, such that blood flow is substantially reduced or inhibited in the mouth of the capture sock device. In some embodiments, the stent is positioned perpendicular to the lumen of the shaft of the capture sock device so that one or more sharp edges of the stent are configured to shred an obstruction in the body channel as the obstruction moves from the body channel into the mouth of the capture sock device. In some embodiments, the system further includes an aspiration device, such that the aspiration device is delivered through the shaft and is configured to apply suction to the obstruction to move the obstruction from the body channel into the mouth of the capture sock device. In some embodiments, the system further includes a trap, such that a proximal end of the trap engages a circumference of a distal portion of the mouth of the capture sock device to create a closed chamber and prevent one or more fragments of the obstruction from moving distally in the body channel. In some embodiments, the stent includes or is formed of a laser cut material to create the one or more sharp edges. In some embodiments, the high-density mesh is selected from the group consisting of: nitinol, Drawn Filled Tube, platinum, gold, tantalum, cobalt chromium, polymer fibers, ePTF, polyurethane, and combinations thereof. In some embodiments, the shaft is a catheter, and the capture sock device is fixedly coupled to a distal end of the catheter. In some embodiments, the system further includes a guidewire, such that the stent is delivered on the guidewire through the shaft of the catheter into the mouth of the capture sock device on the distal end of the catheter. In some embodiments, the obstruction is a large vessel occlusion.

Other features and advantages of the systems, devices, and methodology of the present disclosure will become apparent from the following detailed description of one or more implementations when read in view of the accompanying figures. Neither this summary nor the following detailed description purports to define the invention. The invention is defined by the claims.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

Figure 1:
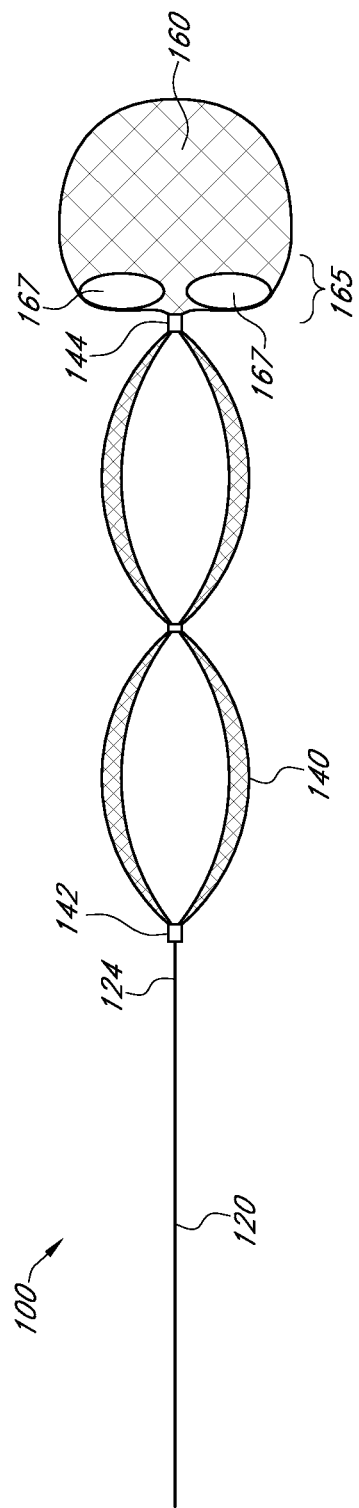
FIG. 1 is a schematic representation of an example of a retriever assembly, according to an embodiment.

The illustrated embodiments are merely examples and are not intended to limit the disclosure. The schematics are drawn to illustrate features and concepts and are not necessarily drawn to scale.

DETAILED DESCRIPTION

In the following detailed description, reference is made to the accompanying drawings that show, by way of illustration, some examples of embodiments in which the disclosure may be practiced. With reference to the above-listed drawings, this section describes particular embodiments and their detailed construction and operation. The embodiments described here are set forth by way of illustration only and not limitation. For example, the sizes, shapes, angles, and relative positions of elements in the drawings are not necessarily drawn to scale and are provided as examples only. Those skilled in the art will recognize in light of the teachings herein that, for example, other embodiments are possible, variations can be made to the example embodiments described herein, and there may be equivalents to the components, parts, or steps that make up the described embodiments. It is to be understood that other embodiments may be utilized, and structural or logical changes may be made, without departing from the scope of the present disclosure.

The terms "operatively coupled," "coupled," "operatively connected," "connected," or "attached" as used herein, may mean directly or indirectly coupled, connected, or attached through one or more intervening components.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The terms "proximal" and "distal" as used herein refer to direction closer to and away from, respectively, an operator (e.g., medical professional, such as surgeon, technician, nurse, or an automated/robotic system) who would insert the systems and devices of the present disclosure into a patient, with the distal end of the device inserted inside a patient's body first. For example, the distal end of the system is inserted inside a patient's body and the opposite end (pointing towards the outside of the patient's body) is the proximal end.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts, for example, requiring manual input. This definition encompasses an automated system in which handheld tools are used but some mechanism of the system functions autonomously, i.e., without human input, to perform a function. Some of the methods described herein may also be robotically assisted or computer/software/machine-instruction controlled. The systems, devices, and methods of the present disclosure are useful in manual procedures and systems, as well as in automated (e.g. robotic) procedures and systems.

For the sake of clarity and conciseness, certain aspects of components or steps of certain embodiments are presented without undue detail where such detail would be apparent to skilled persons in light of the teachings herein and/or where such detail would obfuscate an understanding of more pertinent aspects of the embodiments.

It should be noted that although the present disclosure is particularly useful in clot retrieval within a blood vessel supplying blood to the brain, it is not limited to such blood vessels or to the treatment of ischemic strokes. The methodology and devices of the present disclosure may also be beneficial to other procedures that require removal of an obstruction(s) from the tubular channels of the body (e.g., any blood or lymph vessels). While the description below for convenience will be discussed in reference to blood clots, it shall be understood that it is meant to apply to and cover any obstructions, including foreign objects (such as embolic coils or other objects and instruments accidentally lost and migrated within the vasculature, or left behind during a medical or surgical procedure), vascular obstructions, or particles, such as plaque, tissue fragment, emboli, or thrombi, and the like.

There are many techniques and devices known in the art for removing blockages in the vascular system and other body passageways. Typically, known clot retrievers are inserted into the occluded blood vessel via a catheter. Typically, an expandable wire mesh at the distal end of the retriever grips the clot and is then withdrawn in a proximal direction through the blood vessel through the catheter or sheath. As explained in the background section, such known clot retrievers suffer from a number of shortcomings. The system, devices, and methods described below are designed to solve the above-mentioned shortcomings and problems and improve removal of obstructions from the body passageways.

FIG. 1 illustrates an example of a retriever assembly 100 according to certain embodiments of the present disclosure. The retriever assembly 100 may include a guidewire 120, a retriever 140, and a trap 160. In some embodiments, the components are removably coupled; in other embodiments, the components are fixedly coupled such that a proximal end 142 of the retriever 140 is coupled to the guidewire 120 (e.g., at its distal end 124) and a distal end 144 of the retriever 140 is coupled to a proximal end 165 of the trap 160. As the retriever 140 and the trap 160 are coupled to the same guidewire 120, they may be delivered to the location of the obstruction within the body as a unit, for example, through a micro catheter. The retriever 140 may have various shapes and configurations. In the example of FIG. 1, it is shown as including an arrangement of strands or filaments, each formed as a mesh or braid. It should be understood that the retriever 140 may include one strand or a plurality of strands of the same or different shapes and configurations. For example, in some embodiments, the retriever 140 may include one to five, five to ten, or ten to twenty strands of the same configuration; in other embodiments, the retriever 140 may have several strands of one configuration and several strands of another configuration. The strands of the retriever 140 may be formed with a woven mesh or braid that has variably sized apertures (also referred to as "pores"). In some embodiments, a retriever 140 may have sections of mesh or braid having variation in density of the filaments and may include portions or bands of densely spaced filaments (i.e., lower porosity) and portions or bands that are less dense (i.e., higher porosity). The less dense braid portion may have larger openings in the braid, while the more dense braid portion may have smaller openings in the braid.

Figure 2E:
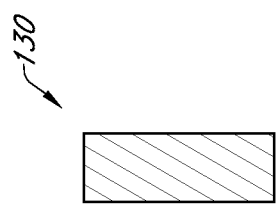
FIG. 2E illustrates an example of an alternative cross-sectional and top view of a strand of a retriever, according to some embodiments.
Figure 2D:
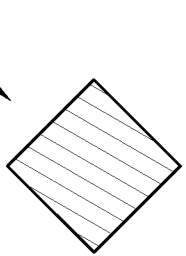
FIG. 2D illustrates an example of an alternative cross-sectional and top view of a strand of a retriever, according to some embodiments.
Figure 2C:
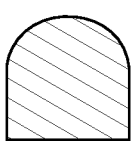
FIG. 2C illustrates an example of an alternative cross-sectional and top view of a strand of a retriever, according to some embodiments.
Figure 2B:
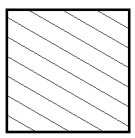
FIG. 2B illustrates an example of an alternative cross-sectional and top view of a strand of a retriever, according to some embodiments.
Figure 2A:
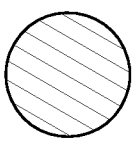
FIG. 2A illustrates an example of an alternative cross-sectional and top view of a strand of a retriever, according to some embodiments.

In some embodiments, at least some or all of the strands are self-expandable. They may be made from super elastic or shape memory alloys. Examples of super elastic or shape memory alloys include, but are not limited to, nitinol, MP35N, stainless steel, cobalt chromium, tantalum, titanium, tungsten or alloys thereof, platinum, polymer fibers, and combinations thereof. The retriever 140 may have a collapsed or compressed configuration such that its diameter fits within a lumen of a delivery catheter, for example, a micro catheter. The strands or filaments of the retriever 140 may capture the obstruction, in this illustration a clot, during retrieval of the device, for example, by cinching and compressing the clot due to the elasticity of the strands. The strands or filaments may be in the form of ribbons or have tubular shape. The retriever 140 may have different shapes, sizes, and/or configurations, including a predetermined shape in a biased configuration. Such predetermined shape may be a generic shape, such as tubular, or can be a custom-made shape. As demonstrated in reference to FIGS. 2A-2E, both a top view and cross-sectional view of a strand 130 of the retriever (such as retriever 140) may have various shapes and configurations, including circular (FIG. 2A), oval, square (FIG. 2B), semi-circle (FIG. 2C), diamond (FIG. 2D), rectangular (FIG. 2E), or any other configuration.

Figure 7:
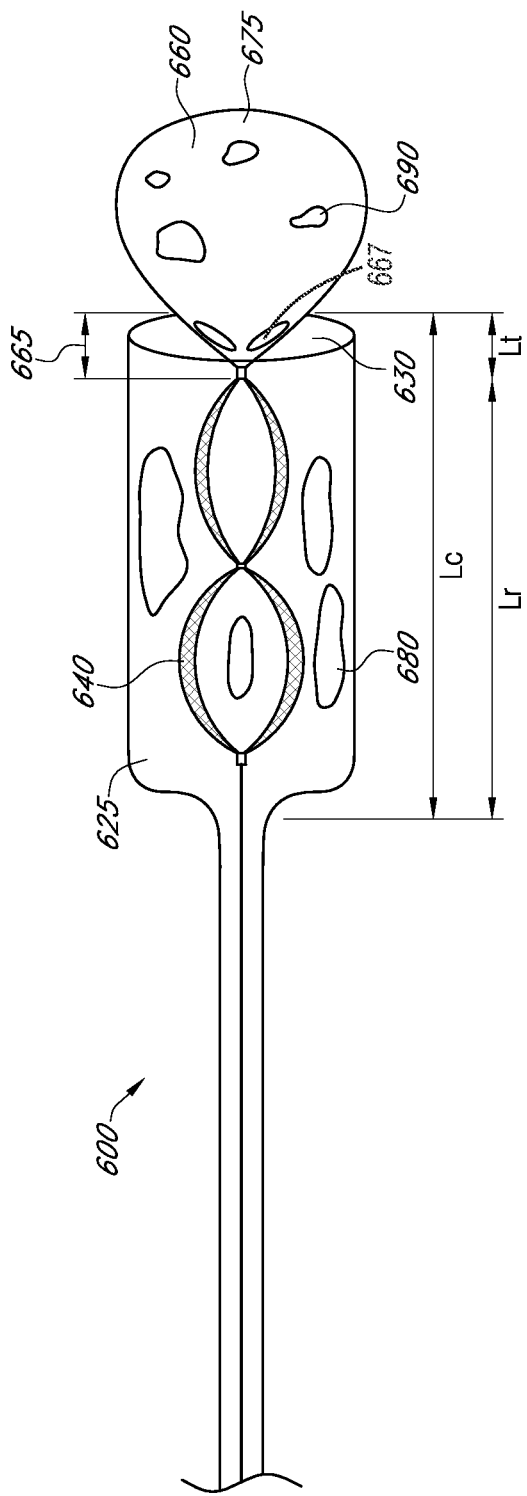
FIG. 7 is a schematic representation of an obstruction removal device, according to some embodiments.

A trap 160 of the embodiment of FIG. 1 is designed to catch and retain any thrombus fragments and prevent them from moving distally or escaping. A trap 160 may also include or be formed of self-expandable mesh or braid made from super elastic or shape memory alloys, such as nitinol. The trap 160 may be also made, for example, from MP35N, stainless steel, cobalt chromium, tantalum, titanium, tungsten or alloys thereof, platinum, polymer fibers, or combinations thereof. The trap 160 may be made of a porous elastic membrane, other braid, or film, and it may have pores of the same or different sizes in different portions of the trap 160. The mesh of the trap 160 may have large enough porosity to allow blood flow and cellular matter to pass through it but small enough to prevent clot fragments from escaping back into the blood stream. For example, in some embodiments, the mesh may have porosity in the range of approximately 120-750 microns and the mesh may include or be formed of 4-120 wires with a diameter of 0.0005"-0.015". In the example of the embodiment of FIG. 1, in the expanded configuration, the trap 160 has a generally spherical or half spherical shape defining an interior region. The proximal end 165 of the trap 160 may have one or more openings 167 or a plurality of openings that are facing the retriever 140 and are larger than the pores of the mesh to allow clot fragments to be captured in the interior region of the trap 160 during clot removal and to prevent them from moving into the blood stream, for example, causing an obstruction(s) to form in distal branches of the vessel. Also, a portion of the trap 160/660 at the proximal end 165/665 may be tapered, for example as shown in FIG. 7. Further details of the configuration and features of the trap 160/660 will be discussed in reference to FIG. 7.

In some embodiments, one or more of a retriever and a trap may include, be formed of, or have a coating of a radiopaque material, or have radiopaque fiducials or markers to permit the user to visualize their respective positions during a procedure, for example using fluoroscopy or other radiation-based methodologies. Alternatively or in combination with the embodiments described above, radiopaque platinum fibers may be included in the mesh or such fibers may include or be formed of other radiopaque metals like tantalum or gold. In addition, the mesh may be constructed of DFT material (Drawn Filled Tube) using nitinol for the outer tube and platinum as the core, making the entire device radiopaque. The size and length of the elements of the assembly may be chosen according to the size of the vessel. For example, different sizes (including the length and the expandable diameter or circumference) of either one or both of the trap and the retriever may be provided, so that an appropriate component best fitting a particular situation may be chosen. Also, in certain embodiments, a retriever assembly may be formed of a trap without a separate retriever. In those embodiments, the trap may be configured to combine the features and functionality of both the retriever and the trap.

Figure 3:
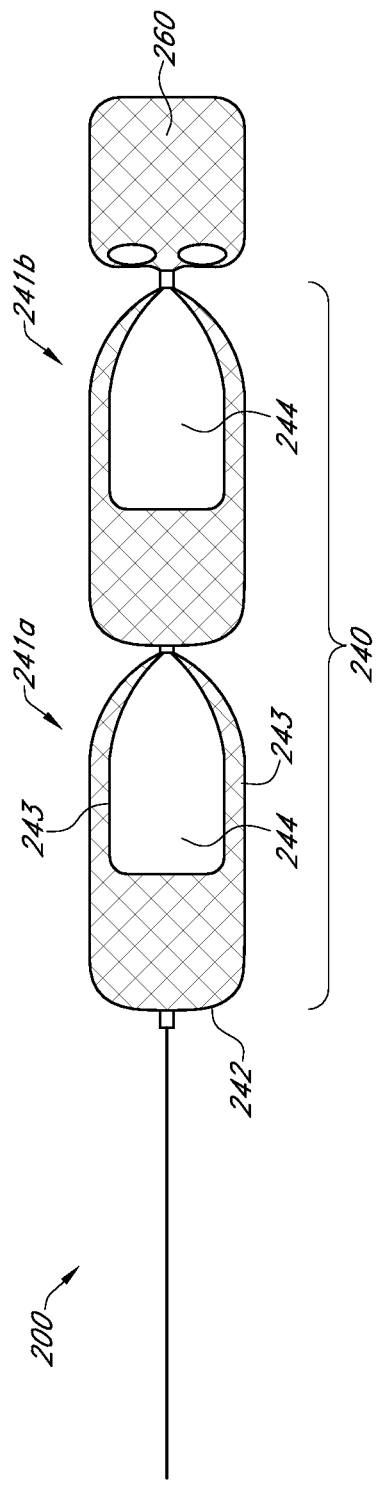
FIG. 3 is a schematic representation of a further example of a retriever assembly with a "hybrid-type" retriever, according to some embodiments.

FIG. 3 demonstrates another embodiment of a retriever assembly 200 of the present disclosure. The retriever 240 of retriever assembly 200 may be referred to as a "hybrid" retriever. Such a retriever 240 may include one or more links (such as links 241a, 241b), such that a portion of a link may be formed from a single strand 242 and another portion of a link may be formed by two or more elongated strands 243. In the illustrated embodiment of FIG. 3, retriever 240 includes two links (241a and 241b), and each link has a single strand portion 242 including or formed of a mesh forming a cup-shaped structure, which is coupled to multiple elongated strands 243 (in this embodiment two strands 243 are shown). As shown in FIG. 3, the gaps, apertures, or openings 244 are formed between or defined by the elongated strands 243. While the links 241a and 241b of the example of FIG. 3 are shown to have the same configuration, it should be understood that in some embodiments, different links may have different configurations. Also, a single strand portion 242 and one or more elongated strands 243 may be formed together as a unit. It should be understood that the structure, relative sizing, and positioning of the elements of the hybrid retriever 200 are not limited to the configuration shown, which is provided as an example only.

Figure 4:
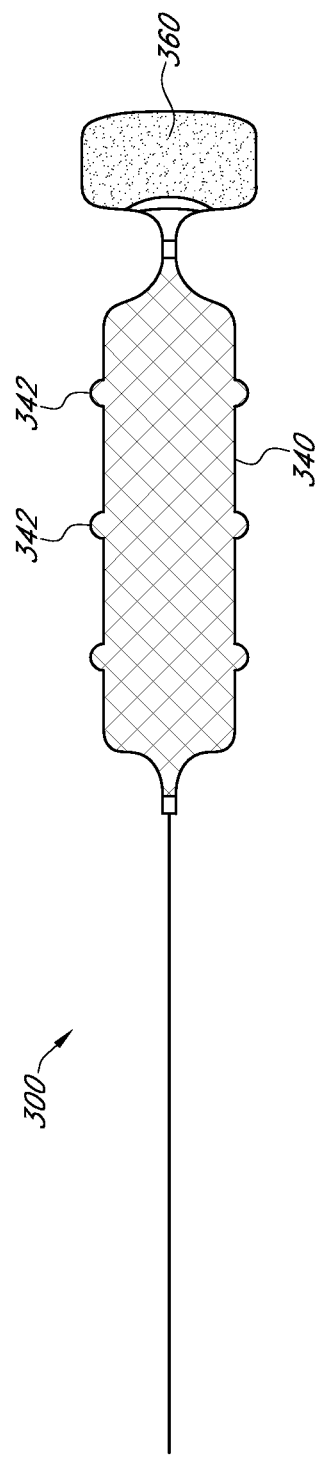
FIG. 4 is a schematic representation of another example of a retriever and a trap, according to some embodiments.

FIG. 4 is an example of yet another embodiment of a retriever assembly 300. In this embodiment, the retriever 300 includes or is formed of a single tubular strand 340 made of a mesh, however, it is formed with a plurality of bumps or protrusions 342 along its surface. These protrusions are designed to engage the clot and assist in retaining the clot in contact with the retriever 300 during retrieval. The trap 360 of the embodiment of FIG. 4 may have a configuration similar to the traps of FIGS. 1-3, or alternatively, it may have a different configuration.

Figure 5:
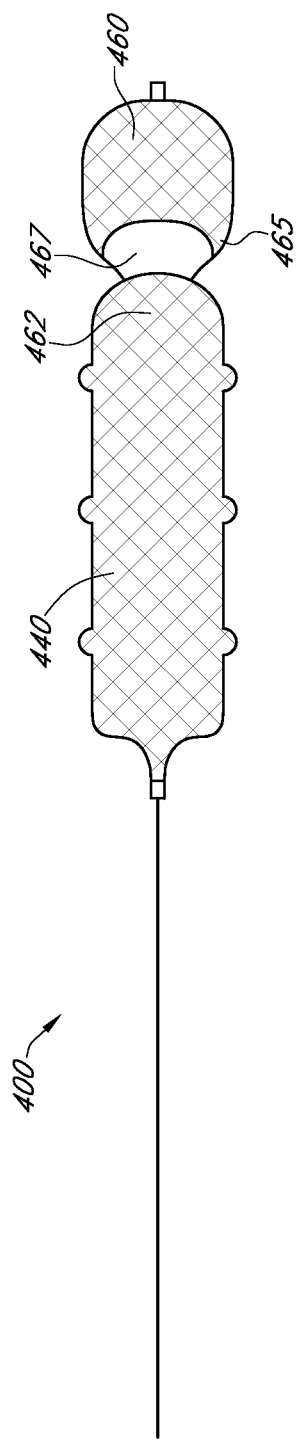
FIG. 5 illustrates still another example of a retriever assembly with an alternative trap configuration, according to some embodiments.

In yet another embodiment depicted in FIG. 5, an alternative design of trap 460 of retriever assembly 400 is provided. Instead of having a generally enclosed configuration with only several small openings (such as openings 167 of FIG. 1) on the proximal side 462 facing the retriever 440, trap 460 may have a cup-like or basket-like shape with one or more large openings 467 at its proximal end 465 facing the retriever 440. As with other embodiments, it is used to prevent dislodged or disrupted portions of the obstruction from migrating beyond or distal of the trap 460 upstream within the blood vessel. When the trap 460 is moved proximally during the withdrawal of the device from the body, the trap 460 captures any fragments or portions of the disrupted clot or other blockage within an interior region of the trap 460.

Figure 6A:
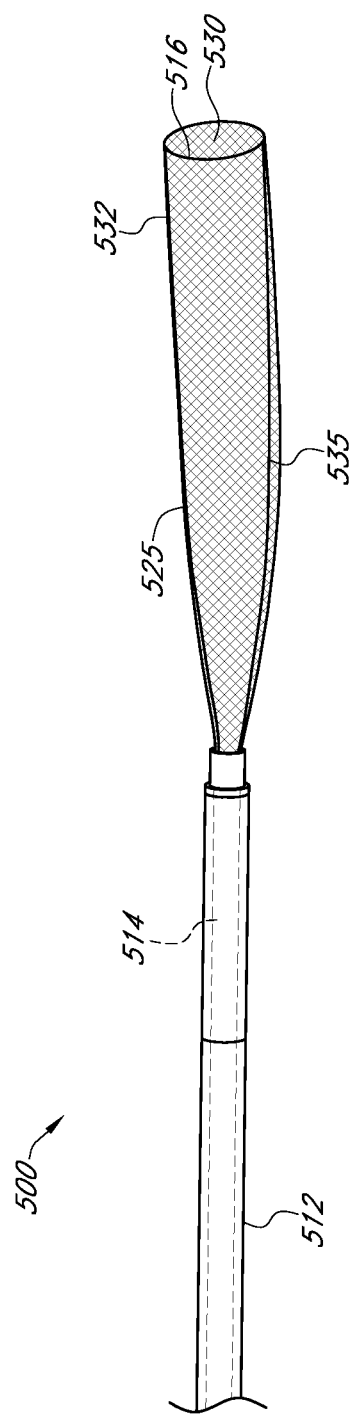
FIG. 6A is a schematic representation of an example of a capture sock device, according to some embodiments.
Figure 6B:
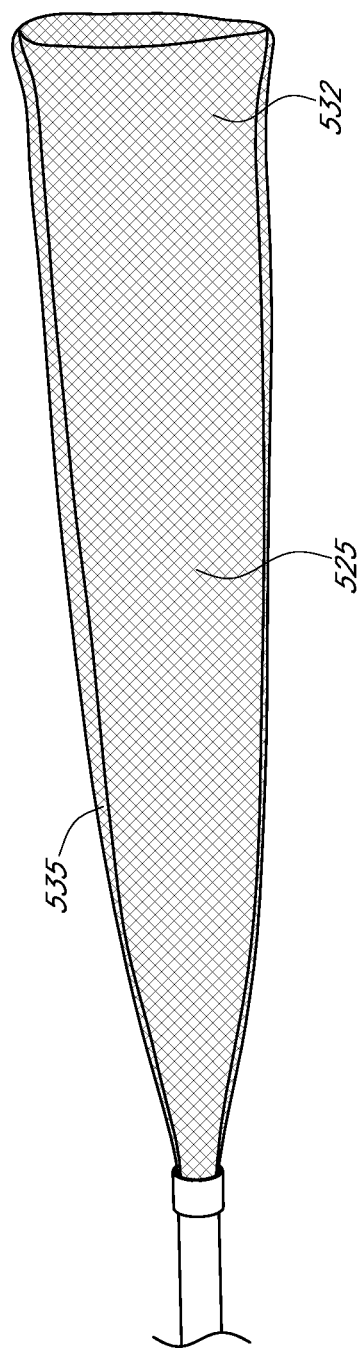
FIG. 6B is a perspective view of a portion of another example of a capture sock device, according to some embodiments.
Figure 6C:
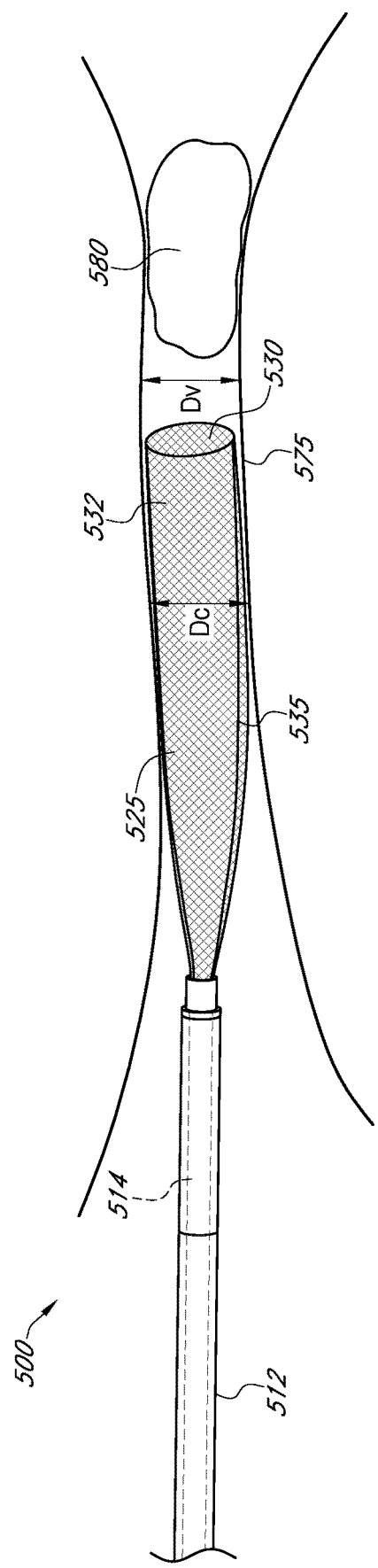
FIG. 6C is a perspective view of a capture sock device sized and configured for use with various aspiration techniques, according to some embodiments.

According to a further aspect, a novel capture sock device or a capture sock member 500 is provided. FIGS. 6A-6C illustrate examples of such a capture sock device 500. In the embodiment of FIG. 6A, the capture sock device 500 comprises a shaft 512 defining a lumen 514, such as a central lumen, and a mouth 525 with a distal opening 530. At least a distal portion 532 of the mouth 525 (or in some embodiments the entire mouth or any portion of the mouth) is folded, for example, on itself creating an inverted configuration or fold 535 with a double layer. In the examples of FIGS. 6A and 6B, the fold 535 extends across the entire mouth 525. It will be understood, however, that the fold 535 may extend along only a portion of the mouth 525. If desirable, more than a double layer may be used in certain embodiments, for example, one to five layers or greater than five layers. Such a folded or inverted configuration provides a smooth and atraumatic edge 516 that is especially beneficial in the implementations of the present disclosure. The inverted/folded configuration provides multiple advantages, including making the distal end or edge 516 of the capture sock device 500 smooth and atraumatic to the vessel wall. In addition, it facilitates an easy and smooth entrance of the proximal end of the trap into the distal opening 530 of the mouth 525 of the capture sock device 500 and avoids any sharp edges that may cause catching of the edges of the trap. As with the retriever and the trap, in some embodiments, the mouth 525 of the capture sock device 500 may be formed of a mesh having large enough porosity to allow blood flow and cells to pass through it but small enough to prevent clot fragments or other obstructions from escaping back into the blood stream. The capture sock device 500 can be braided, weaved, and/or laser cut to create the mesh.

Figure 15A:
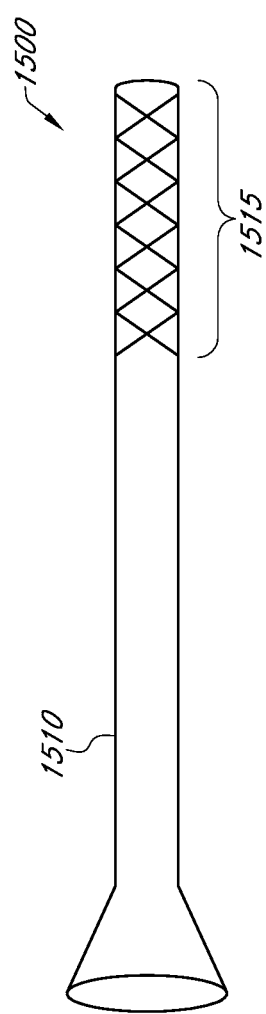
FIG. 15A is a schematic representation of a mechanism for mechanical deployment of a capture sock device, according to some embodiments.
Figure 15B:
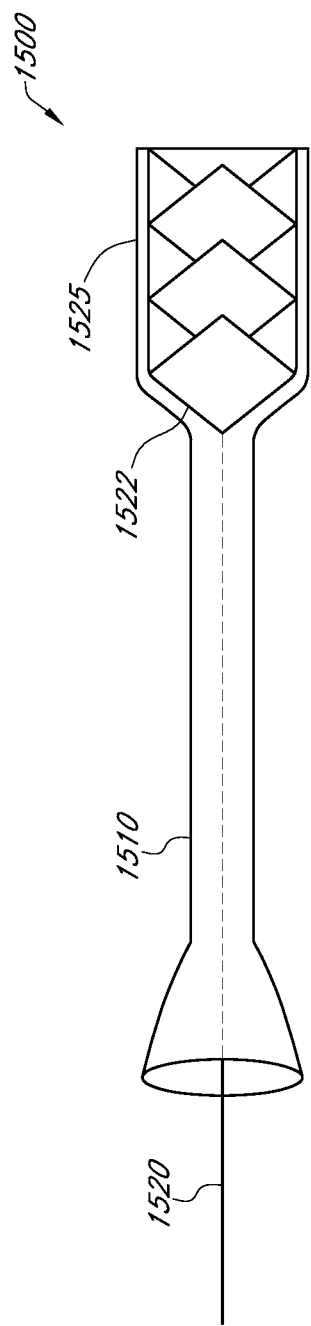
FIG. 15B is a schematic representation of a mechanism for mechanical deployment of a capture sock device, according to some embodiments.
Figure 15C:
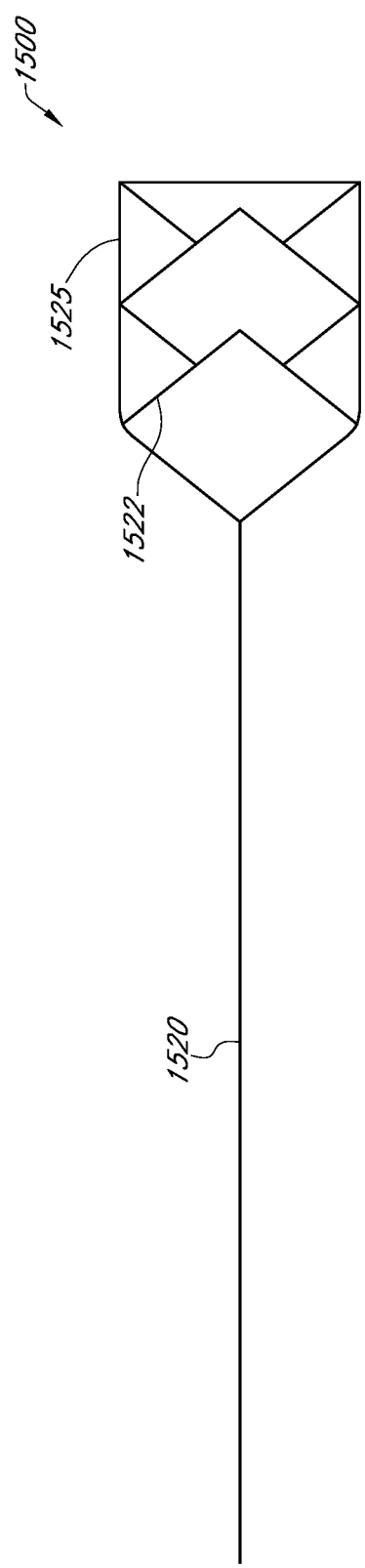
FIG. 15C is a schematic representation of a mechanism for mechanical deployment of a capture sock device, according to some embodiments.

In various embodiments, the capture sock device 500 may be self-expanding. In some such embodiments, the capture sock device 500 may include or be formed of super elastic and/or shape memory alloys, as well as stainless steel, tantalum, platinum and polymer fibers, just to name a few examples. In other embodiments, capture sock device 500 is expanded via mechanical expansion, for example, a balloon expansion or expansion with any type of actuator known in the art may be utilized. For example, as shown in FIGS. 15A-15C, capture sock device 1500 may form part of a distal end 1515 of a reperfusion catheter 1510. The distal end 1515 of reperfusion catheter 1510, comprising the capture sock device 1500, is positioned proximal to the clot or obstruction. As shown in FIGS. 15B and 15C, a stent 1522 or other mechanical actuator is coupled (e.g., removably or fixedly) to a guidewire 1520, delivered through the catheter 1510, and positioned within the capture sock device 1500 to mechanically expand the capture sock device 1500 prior to retrieving, aspirating, or removing the clot or obstruction. In some embodiments, the stent 1522 on the guidewire 1520 is loaded into the catheter 1510 and then delivered to the obstruction site through a delivery sheath.

In some embodiments, one or more struts of the stent 1522 are laser cut so that when the one or more struts sit perpendicular to the lumen of the catheter 1510 and the mouth 1525 of the capture sock device 1500, as shown in FIGS. 15B and 15C, one or more sharp edges of the stent 1522 contact the clot or obstruction as it enters the capture sock device 1500. The sharp edges of stent 1522 function to cut, dice, or otherwise shred the clot or obstruction into smaller pieces to facilitate aspiration and/or removal. The device as shown in FIGS. 15A-15C is particularly useful for large vessel occlusions where the clots tend to be very large.

Returning to FIGS. 6A-6C. In some embodiments as shown in FIG. 6C, capture sock device 500 or any of the embodiments described herein, may be used with an aspiration catheter, aspiration pump device, or other aspiration device, suction device, or means of aspirating) (e.g., syringe) to move the clot or obstruction 580 into the capture sock device 500. For example, an aspiration catheter or device may be advanced through lumen 514 of shaft 512 of capture sock device 500 and used to aspirate one or more obstructions 580 into mouth 525 of capture sock device 500. In some such embodiments, capture sock device 500 includes or is formed of mesh of any of the materials described elsewhere herein or otherwise known in the art having a density that substantially stops or inhibits flow during the obstruction (e.g., clot, thrombus, etc.) retrieval and/or removal process to increase aspiration efficiency. In some embodiments, a circumference or diameter Dv of the body vessel 575 is substantially equal to or slightly larger (e.g., 0.5-1 mm, 1 mm-5 mm, 5 mm-10 mm, or any range or subrange therebetween) than a circumference or diameter Dc of the mouth 525, distal portion 532, or distal opening 530 of the capture sock device 500 to aid in inhibition of blood flow in the capture sock device 500 during aspiration and/or to provide a large compartment for collecting the clot or obstruction during aspiration.

Figure 14:
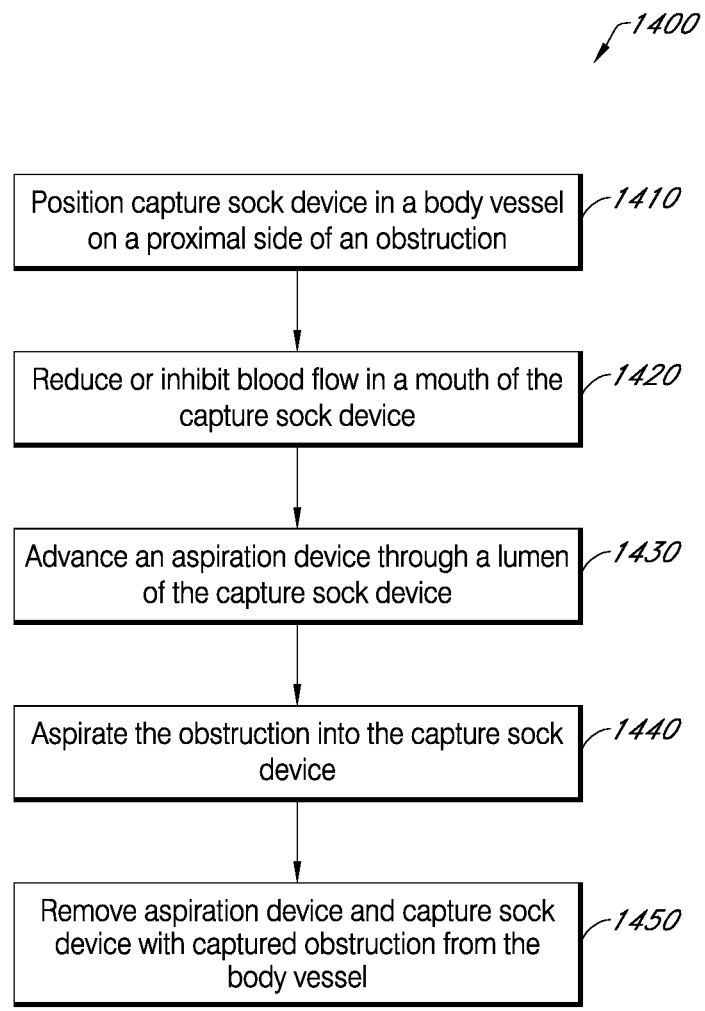
FIG. 14 is a flow chart of a method of using a capture sock device with an aspiration system, according to some embodiments.

A method of using capture sock device 500 of FIG. 6C with an aspiration device or other aspiration means is shown in FIG. 14. Method 1400 functions to enhance removal of obstructions 580 from a body vessel 575 using a capture sock device 500 and an aspiration device or means. Obstruction 580 removal is enhanced by method 1400 at least because (1) a diameter or circumference of a mouth, distal portion, or distal opening of the capture sock device is substantially equal to or slightly smaller (e.g., 0.5-1 mm, 1-5 mm, 5-10 mm, or any range or subrange therebetween) than a diameter or circumference of a diameter of the body vessel; and (2) the mouth of the capture sock device includes or is formed of a material that has a density (i.e., high density) or porosity (i.e., low porosity) sufficient to reduce or inhibit blood flow in the mouth of the capture sock device. Such material may include, but is not limited to, nitinol, DFT material (Drawn Filled Tube), platinum, gold, cobalt chromium, polymer fibers, ePTF, and polyurethane coating with one or more radiopaque elements (e.g., barium sulfate, bismuth compounds, and tungsten) to enhance visualization of the device during procedures. In some embodiments, method 1400 includes: positioning a capture sock device in a body vessel on a proximal side of an obstruction at block 1410; reducing or inhibiting blood flow in a mouth of the capture sock device, such that a diameter or circumference of the mouth of the capture sock device is substantially equal to or slightly less than a diameter or circumference of the body vessel at block 1420; advancing an aspiration device through a lumen of the capture sock device at block 1430; aspirating the obstruction into the capture sock device at block 1440; and removing the aspiration device and capture sock device with the captured obstruction from the body vessel at block 1450.

In some embodiments, the capture sock device 500 may also include, or have a coating, of a radiopaque material, or have radiopaque fiducials or markers to permit the user to visualize their respective positions during a procedure. Alternatively or in combination with the embodiments described above, radiopaque platinum fibers may be included in the mesh or such fibers may include or be formed of other radiopaque metals like tantalum or gold. In addition, the mesh may be constructed of DFT material (Drawn Filled Tube) using nitinol for the outer tube and platinum as the core, making the entire device radiopaque. Also, in some embodiments, the capture sock device 500 may be flared or have an increased circumference at least at the distal end portion 532, or it may be gradually flared along the entire mouth 525 or any portion of the mouth 525 of the capture sock device 500, as shown in FIG. 6B. Such flare provides the advantage of facilitating an easy and smooth entrance of a retriever and a proximal end of a trap into the distal opening 530 of the mouth 525 of the capture sock device 500 (or just a proximal portion of the trap in those embodiments that do not have a retriever).

According to yet a further aspect of the present disclosure, a novel combination of a capture sock device and a trap is provided. The capture sock device and the trap may have complementary configurations designed to solve the problem of the existing devices for retrieval of obstructions, such as clots. One common problem with known devices for retrieval of vascular obstructions (e.g., plaque, emboli, or clots) is that once a filter or similar trapping device captures the clot, it then requires removal often through tortuous anatomy, for example, from the brain to the carotid arteries. As a result of moving through this long and tortuous path, particles or fragments of the captured clot typically break up and escape back into the body, causing additional complications and problems. In fact, quite often in order to successfully remove larger clots, or clots that result in multiple lost fragments, a process of insertion and withdrawal of vascular clot retrievers must be repeated 3-5 times. The proposed combination of the novel capture sock device and a trap solves this problem (whether the trap is used on its own or together with a retriever).

As seen, for example, in FIG. 7, the trap 660 is configured such that its proximal end portion or proximal portion 665, including one or more openings 667, may be tapered or slanted, and the diameter or circumference of the proximal portion 665 is slightly smaller than the internal diameter or circumference of the distal opening 630 of mouth 625 of capture sock device 600, for example, when both the capture sock device 600 and the trap 660 are in their expanded configurations within a body vessel. In some embodiments, a circumference of the proximal portion 665 of the trap 660 may be at least 1 mm to 3 mm smaller than a circumference of the distal portion 532 of the mouth 525 of capture sock device 500 of FIGS. 6A-6B or the circumference of the distal opening 630 of the mouth 625 of the capture sock device 600 in FIG. 7. The above-mentioned difference in the circumferences may be also achieved with the flare at the distal portion 532 of the mouth 525 as shown in FIG. 6B. In other embodiments, a circumference of the proximal portion 665 of the trap 660 may be less than 1 mm, 1 mm, 2 mm, 3 mm, 4 mm, 5 mm, 1 to 5 mm, or 5 to 10 mm smaller than a circumference of the distal portion 532 of mouth 525 of capture sock device 500 or distal opening 630 of mouth 625 of capture sock device 600. This allows the proximal portion 665 of the trap 660 to fit inside the distal opening 630 of the mouth 625 of the capture sock device 600. Altnernatively, in some embodiments a circumference or diameter of the distal end portion or distal portion 675 of the trap 660 may be at least 1 to 3 mm, 1 to 5 mm, or 5 to 10 mm larger than the internal diameter or circumference of the distal end opening 630 of the mouth 625 of the capture sock device 600 so that distal portion 675 of trap 660 is maintained outside of mouth 625 of capture sock device 600. In some embodiments, when the proximal portion 665 of trap 660 is positioned within the distal opening 630 of the mouth 625 of the capture sock device 600, a generally closed chamber is created thereby confining the clot 680 and any fragments 690 within such chamber and preventing any clot 680 and/or clot fragments 690 from migrating into the vasculature during removal of the system.

Alternatively, in some embodiments, a circumference or diameter of proximal portion 665 of trap 660 may be at least 1 to 3 mm, 1 to 5 mm, or 5 to 10 mm larger than the external diameter or circumference of the distal end opening 630 of the mouth 625 of the capture sock device 600 so that distal end opening 630 of mouth 625 of capture sock device 600 fits within distal portion 665 of trap 660 to create a closed chamber to confine clot 680 and any fragments 690 within such chamber.

Further, in some embodiments and procedures (especially when the trap is self-expanding), while it is still desirable to create a closed chamber for capture of the obstruction, it may be also beneficial to ensure that the distal end portion, such as portion 675, of trap 660 remains outside and distal to the mouth 625 of the capture sock device 600, and that it does not collapse and enter into the mouth 625 through the distal end opening 630. Accordingly, in one embodiment of the instant disclosure, the trap 660 is configured to have a variable stiffness along its length. The distal portion 675 of the trap 660 may be constructed to have a higher radial force, i.e., it is stiffer than the proximal portion 665 of the trap 660. The stiffer material forming the distal portion 675 of trap 660 prevents the distal portion 675 of trap 660 from entering into the capture sock device 600 during removal of the capture sock device 600 and the trap 660 from the body channel. The variable stiffness of the trap 660 may be achieved by chemically etching the proximal portion 665 of the trap 660 thereby reducing the diameter of the mesh wires forming the proximal portion 665 of the trap 660 and causing it to have a lower radial force than the distal portion 675, i.e., rendering it less stiff than the distal portion 675. Thus, the proximal portion 665 of the trap 660 is less stiff than the distal portion 675 thereby allowing it to be partially compressed and drawn within the mouth 625 of the capture sock device 600 when trap 660 is moved in a distal direction toward the mouth 625 of the capture sock device 600.

Alternatively or additionally, one or more markers, grooves, or protrusions may be placed on trap 660, for example, at proximal portion 665. These markers may serve as stops to indicate how far the trap 660 may be moved in a proximal direction into the mouth 625 of the capture sock device 660. The markers may be made visible to the human user (e.g., radiopaque, fluorescent, etc.) and/or recognizable by a processor for those implementations that involve automated or robotic systems and procedures.

As a further alternative, according to some embodiments, a length Lc of the mouth 625 of the capture sock device 600 may be chosen such that it facilitates the entrance of the proximal portion 665 of trap 660 into the mouth 625 of the capture sock device 600 while a distal portion 675 of the trap 660 remains outside and distal to the mouth 625 of the capture sock device 600. For example, in some embodiments, a length Lc of the mouth of the capture sock device 600 may be made approximately equal to a combined length of the retriever length Lr and the proximal end portion 665 of the trap 660 length Lt, as shown in FIG. 7. This way, once the retriever assembly is pulled proximally into the mouth 625 of the capture sock device 600, due to its length, the mouth 625 only accommodates the retriever 640 and the proximal end portion 665 of the trap 660, and the remainder of the trap 660 remains distal and outside of the distal end opening 630 of mouth 625. Furthermore, the described benefits of a closed chamber according to the present disclosure may be achieved by using novel features of the capture sock device 600 and the trap 660 without a retriever. In those embodiments where there is no retriever, or where the trap 660 combines the functions of the retriever 640 and the trap 660, the length Lc of the mouth 625 of the capture sock device 600 may be made approximately equal to the length Lt of the proximal end portion 665 of the trap 660.

The trap 660 and the capture sock device 600 may be sold, distributed, marketed, or otherwise provided separately or sold, distributed, marketed, or otherwise offered together as a kit. In various embodiments, as stated elsewhere herein, it is not necessary to have a retriever in addition to a trap, and the trap and/or retriever according to the present disclosure may be used on its own in conjunction with other devices for obstruction removal. For example, it should be noted that a trap according to the present disclosure may be used, for example, in conjunction with thrombectomy devices that use aspiration in the revascularization of patients with acute ischemic stroke. During aspiration procedures for clot removal, clot fragmentation may occur. These clot fragments can migrate distally further into the vasculature causing the operator to repeat the aspiration process one or more times. The trap of the present disclosure aids in capturing these fragments thereby reducing the number of repeated aspirations and the related procedure time.

Figure 13:
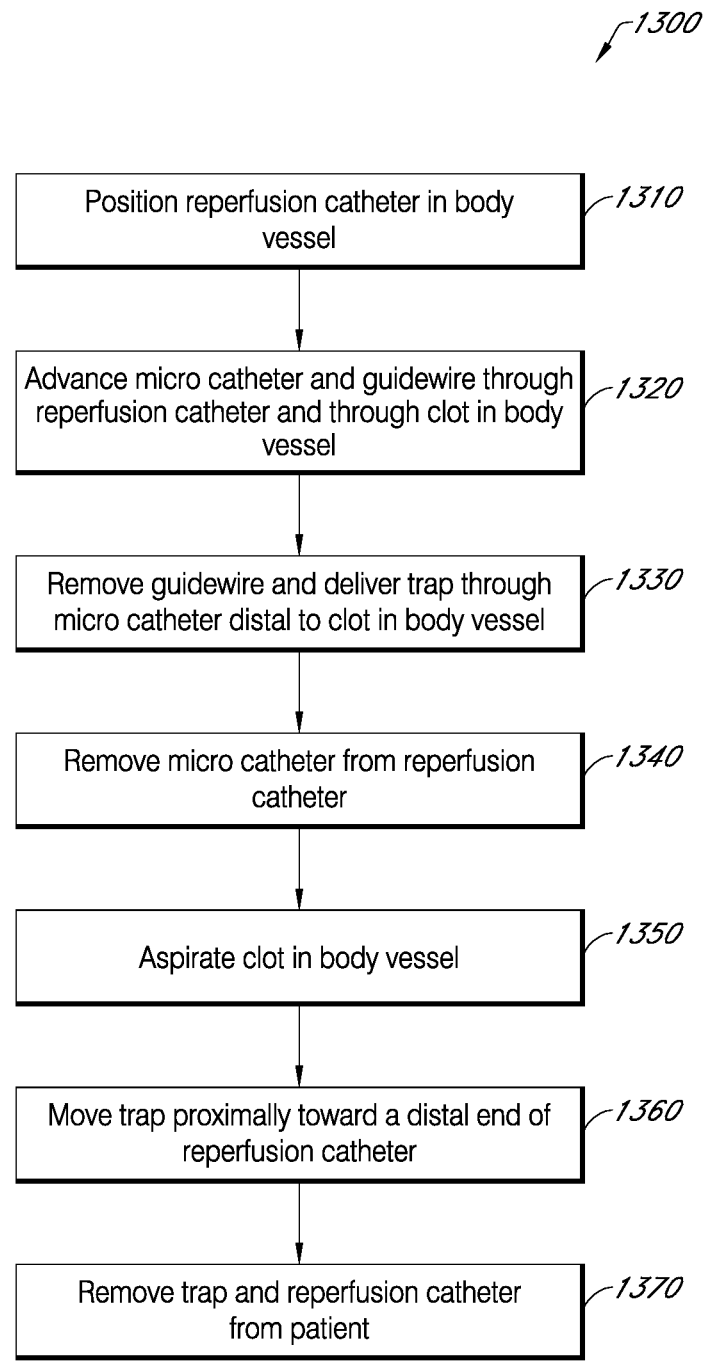
FIG. 13 is a flow chart of a method of using a trap with an aspiration system, according to some embodiments.

As one example, the trap of the present disclosure may be used with reperfusion catheters, aspiration tubing, and/or a vacuum pump, for example those sold by Penumbra, Inc. According to this aspect of the present disclosure, a method of using the trap of the present disclosure in combination with the aspiration system, such as a Penumbra System®, may include steps similar to those described in the "Instructions For Use" (IFU) of the relevant aspiration system and in addition will include the following steps. As shown in the method of FIG. 13, a reperfusion catheter is positioned in a body vessel 1310 and a micro catheter and a guide wire are introduced through the reperfusion catheter to cross into and through the clot 1320. The guide wire is then removed, and the trap is delivered through the micro catheter distal to the clot 1330. Once the trap is in place, the micro catheter may be moved proximally and removed from the reperfusion catheter 1340. Once the micro catheter is removed, the aspiration procedure may be carried out as per the IFU to remove the obstruction 1350. Once the aspiration step is completed, the trap is moved proximally toward the reperfusion catheter such that the proximal end of the trap is positioned inside the distal end of the reperfusion catheter 1360. Once so positioned, the reperfusion catheter and the trap are removed from the patient 1370.

Figure 8:
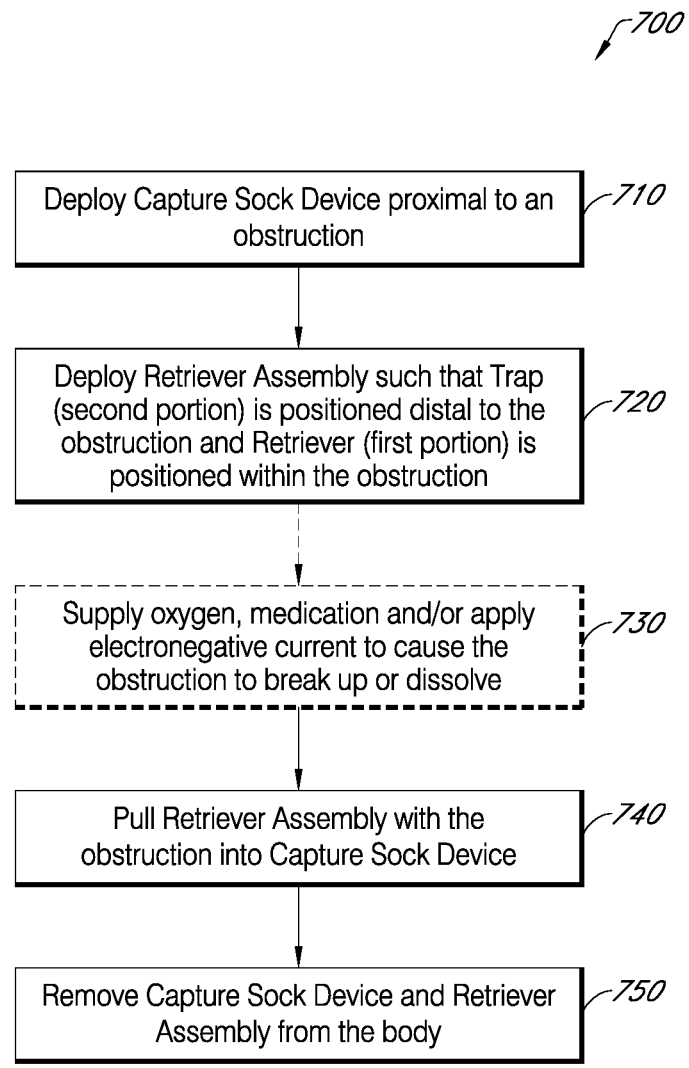
FIG. 8 is a flow chart of a method of using an obstruction removal system, according to some embodiments.

FIG. 8 is a flow chart illustrating an example of a general methodology 700 according to another aspect of the present disclosure. Various steps of the general methodology are also illustrated and will be described in reference to FIGS. 9A-9C. Initially, block 710 includes deploying the capture sock device (for example, capture sock device 500 shown in FIGS. 6A-6B) proximal to the obstruction, for example, a blood clot. The capture sock device may be delivered and deployed using, for example, any standard catheterization techniques. Such techniques are known to those skilled in the art and do not need to be described here in detail. As just an example of such a known technique, in some embodiments, a standard guide catheter may be delivered proximal to the location of the obstruction site. For purposes of restoring the blood flow to the brain, the guide catheter may be delivered approximately 3 inches away from the obstruction (in a proximal direction). The capture sock device may be delivered through the guide catheter and deployed just proximal to the clot. Deployment of the capture sock device may be accomplished, for example, based on its self-expanding nature or using other techniques known in the art (e.g., expansion balloon or actuator).

In block 720, a retriever assembly of any of the embodiments of the present disclosure may be deployed at a desired treatment site (e.g., an obstruction site within the vasculature) with the use of a delivery catheter, for example, a micro catheter. Again, such delivery and deployment may be accomplished using any appropriate catheterization techniques. For example, the micro catheter may be delivered via a guidewire through and past the obstruction site, and the guidewire may be removed. According to the methodology of the present disclosure, the micro catheter may be advanced through the lumen of the capture sock device passing the mouth of the capture sock device and through the obstruction. The retriever assembly may be advanced through the micro catheter until the retriever (which may also be referred to in some embodiments as "a first portion") is positioned inside the obstruction/clot and the distal trap (which may also be referred to in some embodiments as "a second portion") is positioned distal to the clot. In other embodiments, the retriever assembly may only include the trap such that the trap is advanced through the micro catheter until the trap is positioned distal to the clot or obstruction. In some embodiments, the micro catheter is used to compress or collapse the expandable retriever assembly, and when the retriever assembly is moved outside of the catheter, it can assume its biased expanded configuration. Alternatively, in some embodiments, the retriever assembly may be actuated manually and/or automatically to its expanded configuration. The retriever assembly is prevented from expanding until it is in a proper position within the vessel at a clot site. In some implementations, if desired, the retriever assembly may be preloaded into the micro catheter and delivered to the obstruction site as a unit. In these implementations, a distal guidewire tip may be added to the distal end of the trap to assist in navigating the micro catheter containing the retriever assembly through the vasculature. Once the retriever assembly is in the proper position relative to the clot, the micro catheter may be pulled back or at least partially withdrawn, for example, into the lumen of the shaft of the capture sock device which is located proximally to the clot. In embodiments where the retriever and the trap are self-expanding, withdrawing the micro catheter causes the retriever to self-expand within the clot from its collapsed configuration into an expanded configuration and the trap to self-expand distally to the clot from its collapsed configuration to an expanded configuration. As the retriever (the first portion) moves to the expanded configuration, it may assume the overall inner diameter or circumference of the portion of the vessel or other body channel or structure in which it is deployed. Also, as the retriever expands within an obstruction such as a clot, it optimizes its contact with the clot. Deployment of the retriever within a blood clot, typically will begin restoring the blood flow.

Block 730 shown in dotted lines in FIG. 8 is optional and may be used in some of the embodiments/implementations of the methodology of the present disclosure. In some embodiments, electronegative current may be delivered to the clot causing the clot to soften and/or partially or fully dissolve, which assists in a more effective retrieval of the clot. Further details related to the delivery of the electronegative current are described in reference to FIGS. 11 and 12A-12B. The electronegative current may be delivered to the clot (or other obstruction) by operatively connecting the guidewire of the retrieval assembly to a generator. Such delivery may be continued for a period of time sufficient to dissolve or at least partially dissolve the clot. For example, based on the nature and the size of the clot, the electronegative current may be delivered for a period of approximately 5 seconds to 5 minutes. Alternatively or additionally, a flow of oxygen may be delivered to the clot, for example, by simply restoring the blood flow at the obstruction site. Delivery of oxygen has been shown to assist in dissolving, or at least partially dissolving, the clot.

Further, optionally in some implementations, thrombolytics or other clot-dissolving agents/medication may be introduced to dissolve the clot. For example, in some embodiments, the system, devices, and assemblies of the present disclosure may be used in conjunction with clot-dissolving tissue plasminogen activator (tPA).

In block 740 of the method 700, the retriever assembly with the captured clot (and potentially partially dissolved clot) is moved or pulled proximally into the mouth of the capture sock device. For example, it may be pulled into the mouth 825 of the capture sock device 850 such that the retriever 840 is partially collapsed and positioned inside the mouth 825 of the capture sock device 850, and a proximal end 865 of the trap 860 engages the mouth 825, as seen and discussed in more detail in reference to the examples of FIGS. 9A-9C. Finally, in block 750, the capture sock device 850 and the retriever assembly 810 are removed from the body. The novel configuration and engagement of the present capture sock device and retriever assembly provides numerous advantages and solves the problems of known retrievers. Since the clot is fully trapped from all sides, the chances of losing any fragments of the clot into the body channel are prevented or at least substantially reduced. Moreover, even large clots may be retrieved in a single procedure without repeated entry and re-entry into a body channel (such as a blood vessel). The clot is captured and restrained inside the capture sock device from all directions during the entire step of withdrawal.

It will be understood that various steps or a combination of steps of the general methodologies 700, 1300, 1400 may be implemented in some embodiments by computer program instructions. The proposed steps may be substantially automated, which means that some or all of the steps could be performed automatically, for example, by a processor or other computing device. It does not exclude, however, that the user may intervene and participate, for example, by giving an alternative command through a user interface, or override the automated command. The methodology of the present disclosure may be also implemented using robotic systems having master/slave relationship where a physician, surgeon, or other medical professional directs or controls movements and operation of the tools attached to the robotic arms of the robotic system.

Figure 9A:
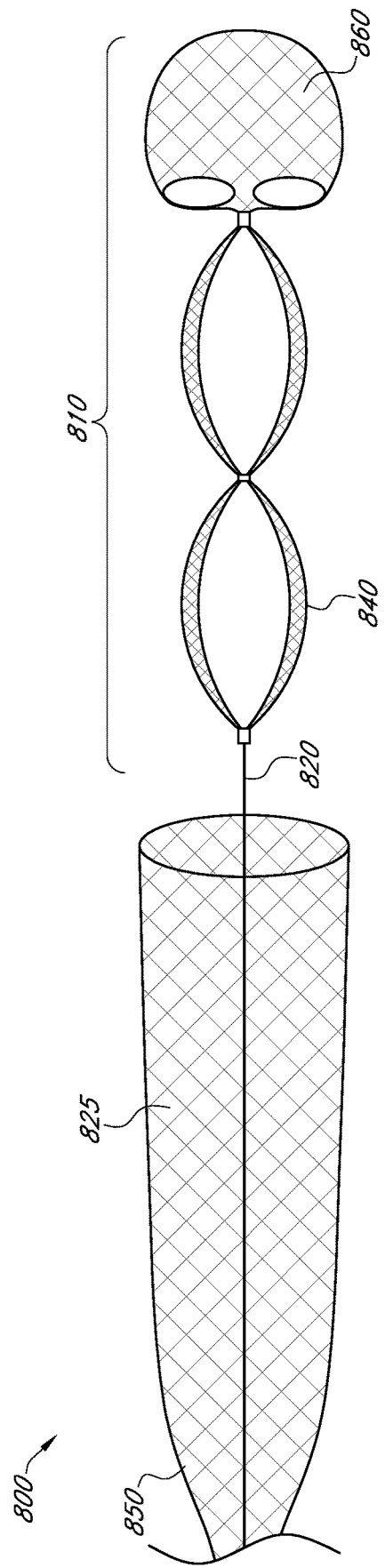
FIG. 9A is a schematic representation of an example of an obstruction removal system for use according to the method of FIG. 8.

FIG. 9A illustrates an example of the components of the system 800 of the present disclosure according to some embodiments. The obstruction removal system 800 of this embodiment includes a capture sock device 850 having a mouth 825. The system 800 also includes a retriever assembly 810 that may include a guidewire 820, a retriever 840, and a trap 860. Each of the above components may have any features and configurations as described above in reference to FIGS. 1-7. In some embodiments, the capture sock device 850 may have an inverted or folded layer configuration, while in some embodiments, it may have a single layer or multiple layer configuration. According to some embodiments, the retriever assembly may include only a guidewire and a trap, where the trap has functionality of both the retriever and the trap.

Figure 9B:
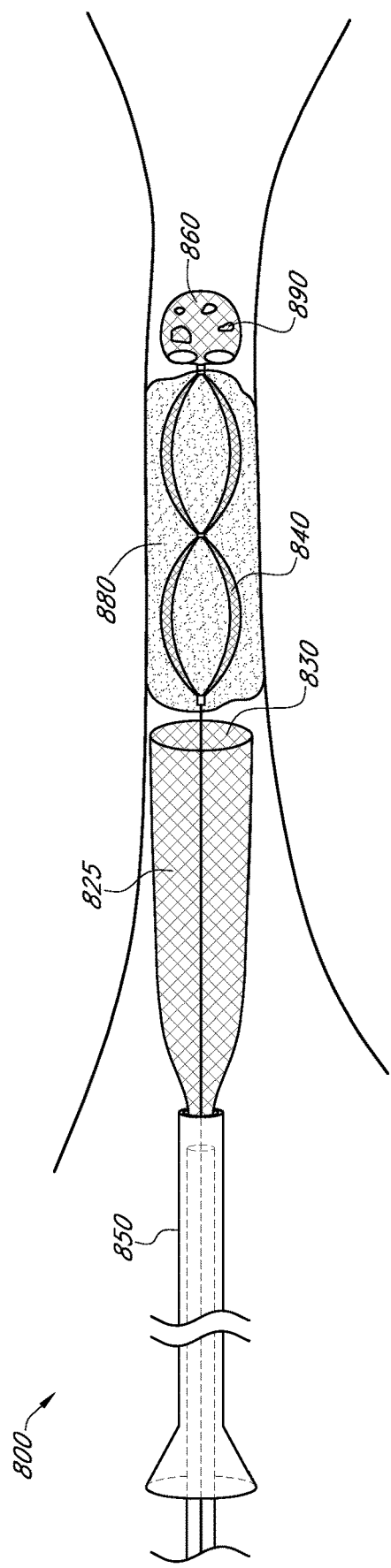
FIG. 9B illustrates the system of FIG. 9A with the retrieval assembly deployed and engaging an obstruction, such as clot.

FIG. 9B illustrates the system 800 of FIG. 9A with the retrieval assembly 810 deployed and engaging an obstruction, such as blood clot 880. FIG. 9B captures an example of a moment in time during the initial stage of block 740 of the method 700 of FIG. 8; it shows the retriever 840 with the captured clot 880 being pulled back towards the distal opening 830 of the mouth 825 of the capture sock device 850 while the distally positioned trap 860 is capturing any loose clot fragments 890.

Figure 9C:
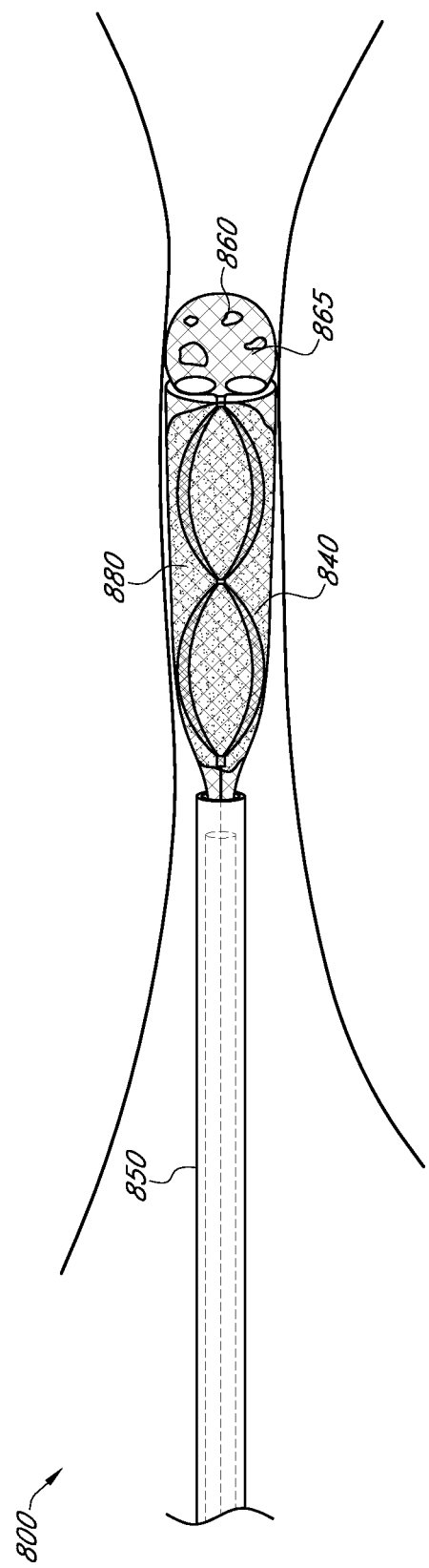
FIG. 9C illustrates the system of FIG. 9A when the retriever with the obstruction is captured inside the capture sock device.

FIG. 9C illustrates the system of FIG. 9A when the retriever 840 with the obstruction 880 is captured inside the capture sock device 850, which represents an example of a moment in time during completion of block 740 of the method 700 of FIG. 8. As seen in FIGS. 7 and 9C, a proximal end portion 665 (865) of the trap 660 (860) is engaged with the mouth 625 (825) of the capture sock device 600 (800) at the distal opening 630 (830) such that the obstruction and all loose fragments are captured and enclosed by the obstruction removal system 800 of the present disclosure.

Figure 10:
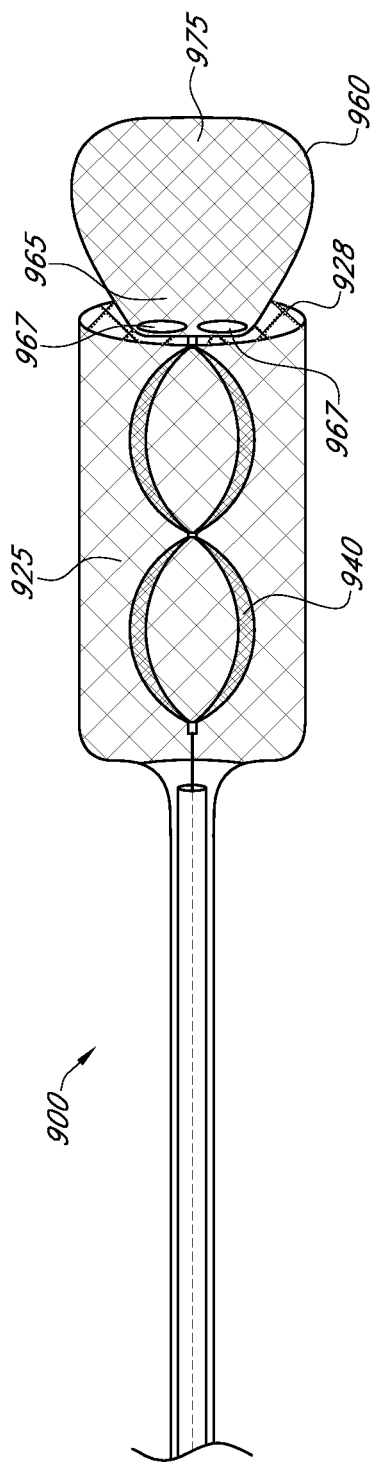
FIG. 10 is another example of an obstruction removal system and the positioning of components of the system for the withdrawal of the system from the body, according to some embodiments.

FIG. 10 illustrates another example of the components of the obstruction removal device 900 and their relative positioning and fit when the retrieval assembly is partially withdrawn into the capture sock device 900 and the trap 960 engages the mouth 925 of the capture sock device 900. For the sake of clarity of the view of the components of the system, the clot and clot fragments are not shown. As seen in FIG. 10, a portion (such as proximal end portion 965) of trap 960 is tapered and may fit inside and engage the distal end portion 928 of mouth 925 of the capture sock device while retriever 940 (with the captured obstruction) fits fully inside the mouth 925. Also, a circumference of the distal end portion 975 of the trap 960 is larger (e.g., 1-3 mm) than the circumference of the distal end portion 928 of the mouth 925 of the capture sock device 900. While this embodiment does not show a flare or an enlarged circumference of the distal end portion 928 of the mouth, it should be understood that it may have a flare similar to the flare of FIG. 6B. As illustrated, the components of the obstruction removal system are sized and configured to create a closed chamber for capturing and fully enclosing the obstruction and any of its potential fragments that may be dislodged during withdrawal of the system. While FIG. 10 illustrates the fit of the components of the example of the obstruction removal system including a capture sock device, a retriever, and a trap, it should be understood that in the implementations including only a capture sock device and a trap, various features of the trap, as previously described, may be combined with various features of the capture sock device to provide a closed chamber similar to the closed chamber shown in FIG. 10.

Figure 11:
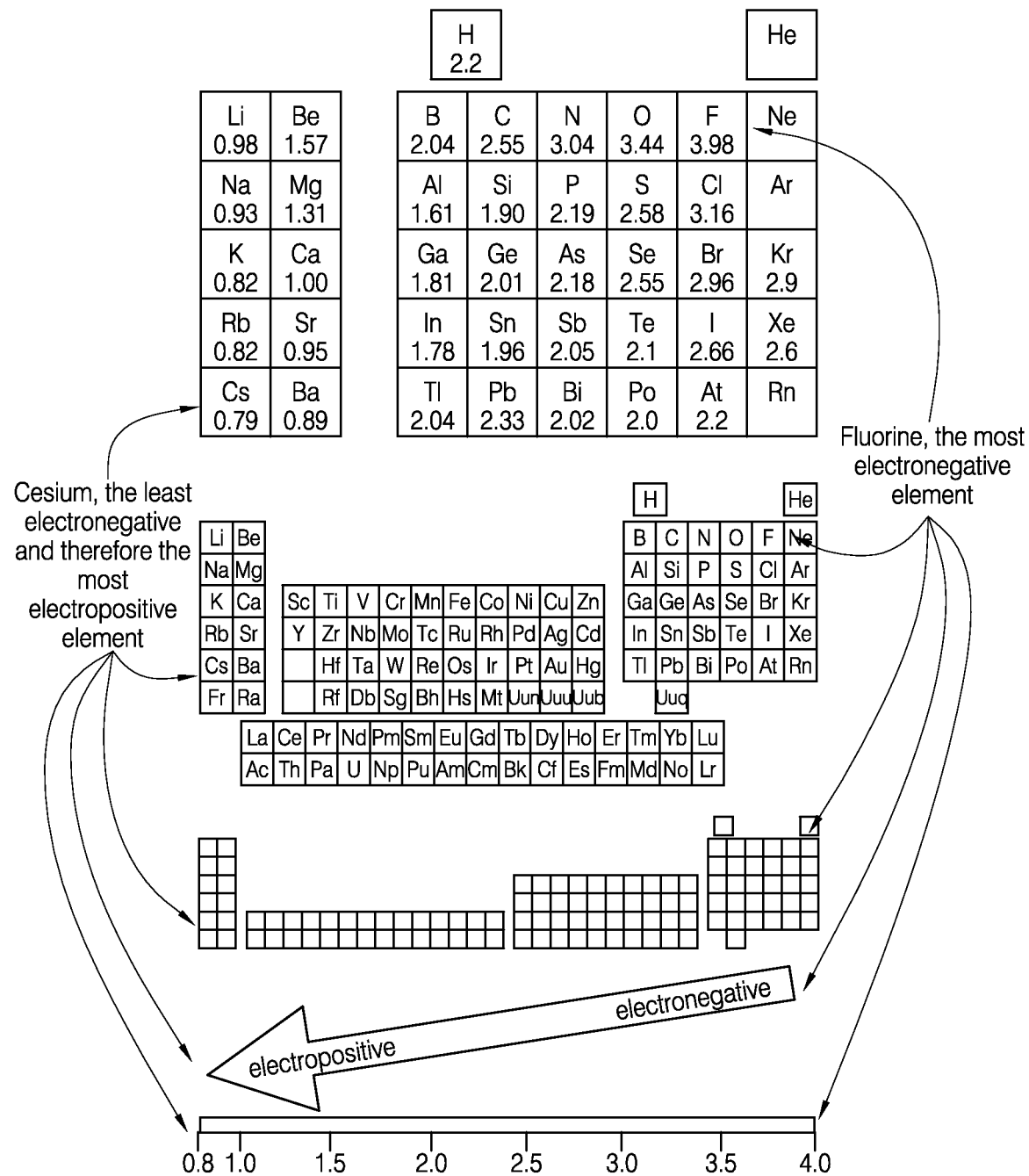
FIG. 11 is a Periodic Table (by Pauling scale) of electropositive and electronegative elements that may be utilized in the methodology of the present disclosure.

FIG. 11 illustrates the Periodic Table showing electronegativity by Pauling scale and identifies electronegative elements that may be utilized in some embodiments of the disclosed methodology according to an optional block 740. It has been discovered that supplying electronegative current to a blood clot may assist in dissolving or partially dissolving the clot. The length of time for supply of the electronegative current will depend, among other things, on a size and/or composition of the clot or obstruction. For example, for a clot of approximately 1 cm, electronegative current may be supplied for approximately one minute. For obstructions of other sizes or nature, electronegative current may be supplied for a period of, for example, 5 seconds to 5 minutes prior to its withdrawal from the blood vessel. As seen in FIG. 11, Fluorine is the most electronegative element and Oxygen is positioned next to Fluorine in the periodic table indicating that is also possesses high electronegativity. Therefore, supplying oxygen to the clot prior to its removal or retrieval from the body may also assist in at least partially dissolving the clot.

Figure 12A:
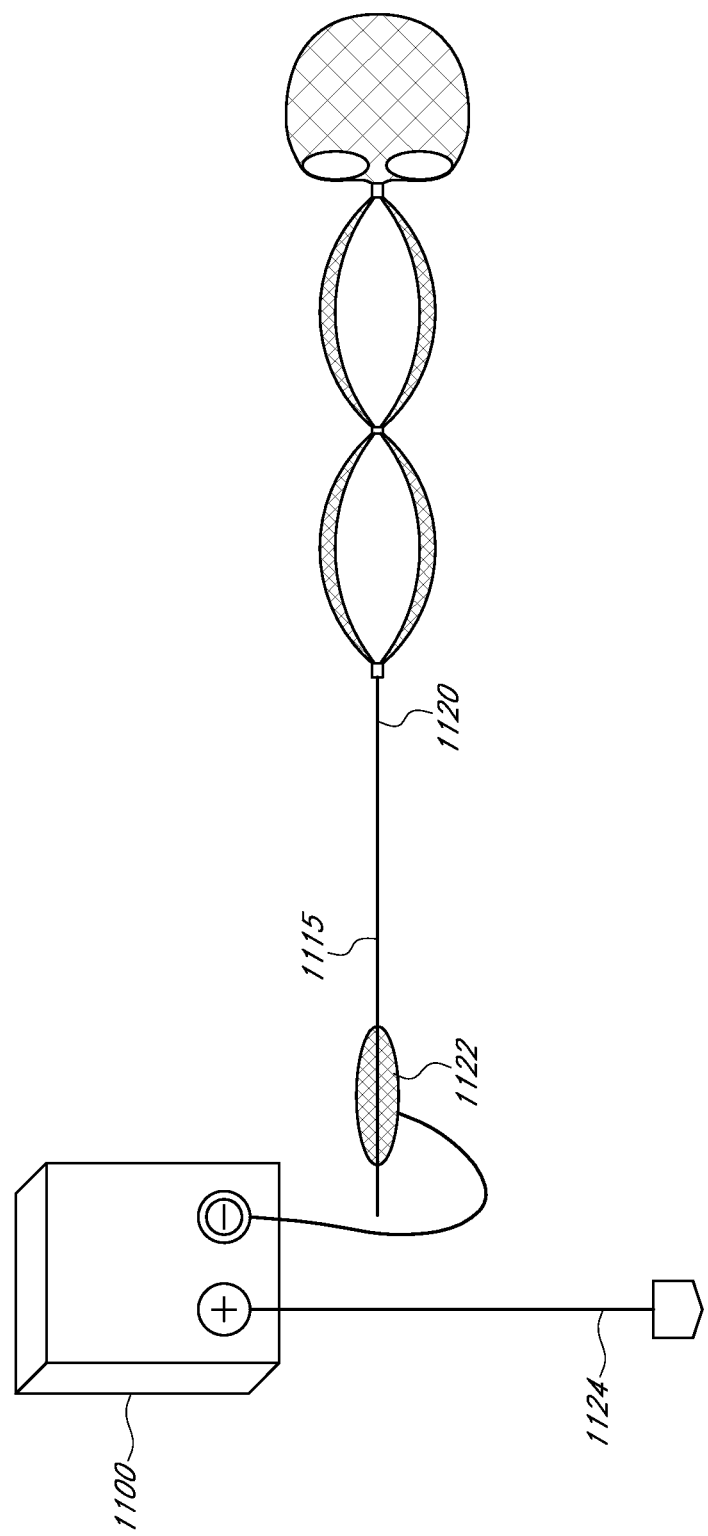
FIG. 12A is schematic representation of a generator that may be used for supplying electronegative current to an obstruction site, according to some embodiments.
Figure 12B:
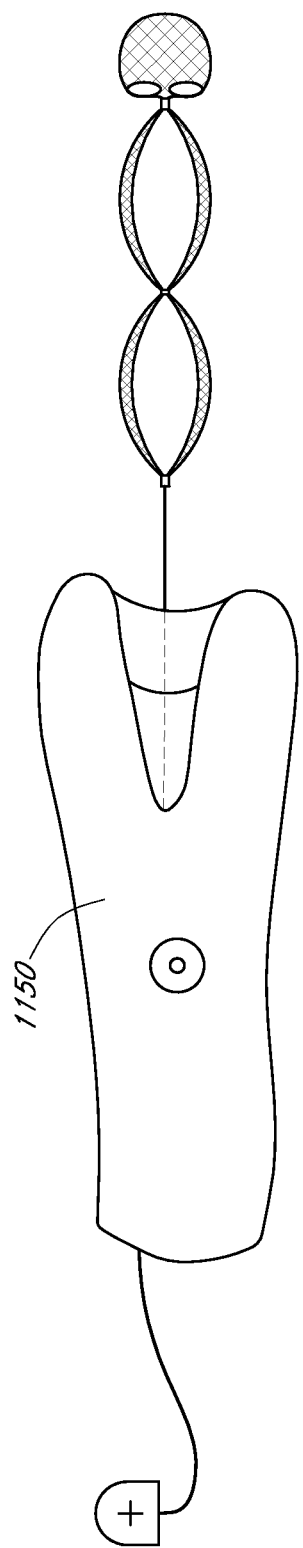
FIG. 12B is schematic representation of a handheld generator that may be used for supplying electronegative current to an obstruction site, according to some embodiments.

FIGS. 12A and 12B are schematic representations of examples of generators that may be used for supplying electronegative current to an obstruction site according to some of the embodiments. FIG. 12A provides an example of a generator 1100 that may be placed, for example, on a table next to a patient undergoing a blockage removal procedure, while FIG. 12B provides an example of a hand-held device 1150 that a physician may hold or alternatively, may place on a table or other surface, for example, near a patient. In the embodiment illustrated in FIG. 12A, a proximal end 1115 of the guidewire 1120 of the retriever assembly 1110 may be attached to a generator clip 1122 and a positive/ground patch 1124 may be attached to the patient.

In operation, once the retriever assembly is deployed and the obstruction (e.g., clot) is engaged by the retriever, the generator is turned on to deliver electronegative current to the blood clot or other obstruction causing the clot to soften and dissolve for a more effective retrieval. Once the energy cycle is complete, the clip may be disconnected from the wire and the retriever assembly may be pulled back into the capture sock device until the proximal end of the trap enters the mouth of the capture sock device, as described in reference to the methods of FIG. 8.

Although while it may be suggested that the systems, devices, and assemblies of the present disclosure may include particular components arranged in a particular configuration, it is understood that this is for the purposes of example. In various implementations, the system, devices, and assemblies may include any number of components (including a particular device may comprise a number of components or elements, or several components may be combined and presented as a single unit) arranged in different configurations without departing from the scope of the present disclosure. For example, in those embodiments where the retriever assembly includes only a trap that functions as both the retriever and the trap, the blocks of general methodology 700 are adjusted accordingly, for example, such that any reference to a retriever is eliminated or substituted for a relevant feature of the trap.

It is to be understood that other embodiments than those described above may be utilized and structural or logical changes may be made without departing from the scope of the present disclosure. The illustrated and described embodiments of the disclosure are susceptible to various modifications and alternative forms, and it should be understood that the disclosure as generally disclosed herein, as well as the specific embodiments described herein, are not limited to the particular forms or methods disclosed, and that many other embodiments are possible within the spirit and the scope of the present disclosure. Moreover, although individual features of one embodiment may be discussed herein or shown in the drawings of one embodiment and not in other embodiments, it should be apparent that individual features of one embodiment may be combined with one or more features of another embodiment or features from a plurality of embodiments. By way of a non-limiting example, it will be appreciated by those skilled in the art that particular features or characteristics described in reference to one figure or embodiment may be combined with features or characteristics described in another figure or embodiment.

It will be apparent that the number of steps that are utilized for such methods are not limited to those described elsewhere herein. Also, the methods do not require that all the described steps are present. Although the methodology is described above as discrete steps, one or more steps may be added, combined or even deleted, without departing from the intended functionality of the embodiments. The steps can be performed in a different order or the steps may be shared between more than one processor, for example. It will also be apparent that the method described above may be performed in a partially or substantially automated fashion, including performed using robotic systems. It will also be apparent that the methods described above may be performed manually, or they may be partially or substantially automated, including performed using robotic systems. As will be appreciated by those skilled in the art, the methods of the present disclosure may be embodied, at least in part, in software and carried out in a computer system or other data processing system. Therefore, in some exemplary embodiments hardware may be used in combination with software instructions to implement the present disclosure, including the methodology provided.

As used in the description and claims, the singular form "a", "an" and "the" include both singular and plural references unless the context clearly dictates otherwise. For example, the term "obstruction" may include, and is contemplated to include, a plurality of obstructions. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device or system.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Applicant regards the subject matter of the disclosure to include all combinations and sub-combinations of the various elements, features, functions, and/or properties disclosed herein. The Detailed Description, therefore, is not to be taken in a limiting sense, and the scope of the present disclosure is defined by the appended claims.

What is claimed is:

1. An obstruction removal system comprising:
a capture sock device comprising a mouth coupled to a shaft defining a lumen; and
a trap coupled to a distal end of a guidewire, the trap comprising one or more openings facing the capture sock device, wherein the trap is self-expanding and comprises a proximal portion and a distal portion, and wherein the distal portion is more rigid than the proximal portion,
wherein any one or more of the capture sock device and the trap are movable between a collapsed configuration and an expanded configuration, and
wherein the capture sock device and the trap are sized and configured, when positioned inside a body channel, such that the trap with a captured obstruction may be withdrawn into the mouth of the capture sock device and the trap may engage with the mouth of the capture sock device to form a closed chamber, the closed chamber preventing the obstruction or a fragment of the obstruction from migrating into the body channel during removal of the capture sock device and the trap from the body channel.

2. The obstruction removal system of claim 1, wherein the mouth of the capture sock device has a distal end portion with a distal opening and a circumference at the distal opening, and wherein a proximal portion of the trap is configured to engage the circumference of the distal opening of the mouth of the capture sock device.

3. The obstruction removal system of claim 1, wherein the proximal portion of the trap is tapered.

4. The obstruction removal system of claim 3, wherein the proximal portion of the trap, when positioned inside the body channel, is sized and configured to be smaller than the circumference of the distal opening of the mouth of the capture sock device causing it to fit inside the mouth while a distal portion of the trap is sized and configured to be larger than the circumference of the distal opening of the mouth of the capture sock device causing it to remain outside and distal to the mouth.

5. The obstruction removal system of claim 1, wherein any one or more of the capture sock device and the trap are self-expandable when unconstrained.

6. The obstruction removal system of claim 1, wherein any one or more of the capture sock device and the trap comprises a mesh or braided structure.

7. The obstruction removal system of claim 1, wherein at least a distal portion of the mouth of the capture sock device comprises a flare.

8. The obstruction removal system of claim 1, wherein, in the expanded configuration, the mouth of the capture sock device is configured to contact a wall of the body channel.

9. The obstruction removal system of claim 1, wherein the mouth of the capture sock device comprises a mesh being folded to create two layers at the distal opening of the mouth.

10. An obstruction removal system comprising:
a capture sock device comprising a mouth coupled to a shaft defining a lumen; and
a retriever assembly comprising:
a retriever configured to capture an obstruction, a proximal end of the retriever coupled to a distal end of a guidewire; and
a trap coupled to a distal end of the retriever, the trap comprising one or more openings facing the retriever, wherein the trap is self-expanding and comprises a proximal portion and a distal portion, and wherein the distal portion is more rigid than the proximal portion,
wherein any one or more of the capture sock device, the retriever, and the trap are movable between a collapsed configuration and an expanded configuration, and
wherein the capture sock device and the retriever assembly are sized and configured, when positioned inside a body channel, such that the retriever with a captured obstruction may be withdrawn into the mouth of the capture sock device and the trap may engage with the mouth of the capture sock device to form a closed chamber, the closed chamber preventing the obstruction or a fragment of the obstruction from migrating into the body channel during removal of the capture sock device and the retriever assembly from the body channel.

11. The obstruction removal system of claim 10, wherein the mouth of the capture sock device has a distal end portion with a distal opening and a circumference at the distal opening, and wherein a proximal portion of the trap is configured to engage the circumference of the distal opening of the mouth of the capture sock device.

12. The obstruction removal system of claim 11, wherein the proximal portion of the trap, when positioned inside the body channel, is sized and configured to be smaller than the circumference of the distal opening of the mouth of the capture sock device causing it to fit inside the mouth while a distal portion of the trap is sized and configured to be larger than the circumference of the distal opening of the mouth of the capture sock device causing it to remain outside and distal to the mouth.

13. The obstruction removal system of claim 10, wherein the proximal portion of the trap is tapered.

14. The obstruction removal system of claim 10, wherein any one or more of the capture sock device, the retriever, and the trap are self-expandable when unconstrained.

15. The obstruction removal system of claim 10, wherein any one or more of the capture sock device, the retriever, and the trap comprises a mesh or braided structure.

16. The obstruction removal system of claim 10, wherein at least a distal portion of the mouth of the capture sock device comprises a flare.

17. A method for removing obstructions from a body channel, comprising:
deploying a capture sock device, comprising a mouth, proximal to an obstruction site in a body channel;
deploying a retriever assembly distally to the capture sock device such that a retriever of the retriever assembly is positioned in the obstruction site and a trap of the retriever assembly is positioned distally to the obstruction site, the trap configured to prevent the obstruction or a fragment of the obstruction from moving distally to the trap, wherein deploying the retriever assembly comprises the trap self-expanding from a collapsed configuration to an expanded configuration, wherein the trap comprises a proximal portion and a distal portion, and wherein the distal portion is more rigid than the proximal portion;

moving the retriever assembly with the obstruction captured therein into the capture sock device, thereby creating a closed chamber preventing the obstruction or the fragment of the obstruction from migrating into the body channel during removal of the capture sock device and the retriever assembly from the body channel; and removing the capture sock device and the retriever assembly from the body channel.

18. The method of claim 17, wherein the proximal portion of the trap is tapered.

19. The method of claim 17, wherein any one or more of the capture sock device and the trap comprises a mesh or braided structure.

20. The method of claim 17, wherein the mouth of the capture sock device comprises a mesh being folded to create two layers at the distal opening of the mouth.

* * * * *